(12) United States Patent
Flores et al.

(10) Patent No.: US 7,741,285 B2
(45) Date of Patent: Jun. 22, 2010

(54) APO-2 LIGAND/TRAIL FORMULATIONS

(75) Inventors: Heather Flores, Hayward, CA (US); Tanya P. Lin, Bronx, NY (US); Timothy C. Matthews, Millbrae, CA (US); Roger Pai, Los Altos, CA (US); Zahra Shahrokh, Weston, MA (US)

(73) Assignee: Genentech, Inc., South San Francisco, CA (US)

( * ) Notice: Subject to any disclaimer, the term of this patent is extended or adjusted under 35 U.S.C. 154(b) by 210 days.

(21) Appl. No.: 11/136,842

(22) Filed: May 24, 2005

(65) Prior Publication Data

US 2006/0009387 A1    Jan. 12, 2006

Related U.S. Application Data

(63) Continuation-in-part of application No. 10/771,254, filed on Feb. 3, 2004, now abandoned, which is a continuation-in-part of application No. PCT/US02/36251, filed on Nov. 12, 2002.

(51) Int. Cl.
*A61K 38/00* (2006.01)

(52) U.S. Cl. .................................. 514/12; 512/2
(58) Field of Classification Search ........................ None
See application file for complete search history.

(56) References Cited

U.S. PATENT DOCUMENTS

| | | | |
|---|---|---|---|
| 5,610,279 A | 3/1997 | Brockhaus et al. | |
| 5,763,223 A | 6/1998 | Wiley et al. | |
| 5,808,029 A | 9/1998 | Brockhaus et al. | |
| 6,030,945 A | 2/2000 | Ashkenazi et al. | |
| 6,284,236 B1 | 9/2001 | Wiley et al. | |
| 6,541,606 B2 | 4/2003 | Margolin et al. | |
| 2007/0161564 A1* | 7/2007 | Ashkenazi et al. | ............ 514/12 |

FOREIGN PATENT DOCUMENTS

| | | |
|---|---|---|
| EP | 870827 | 10/1998 |
| WO | WO97/01633 | 1/1997 |
| WO | WO97/25428 | 7/1997 |
| WO | WO98/18921 | 7/1998 |
| WO | WO98/28426 | 7/1998 |
| WO | WO98/32856 | 7/1998 |
| WO | WO98/35986 | 8/1998 |
| WO | WO98/41629 | 9/1998 |
| WO | WO98/46643 | 10/1998 |
| WO | WO98/46751 | 10/1998 |
| WO | WO98/51793 | 11/1998 |
| WO | WO99/02653 | 1/1999 |
| WO | WO99/09165 | 2/1999 |

(Continued)

OTHER PUBLICATIONS

Cha et al., Acta Crystallogr D Biol Crystallogr. May 1999;55(Pt 5):1101-4.*

(Continued)

*Primary Examiner*—Cherie M Woodward
(74) *Attorney, Agent, or Firm*—Diane Marschang, Esq.; Ginger R. Dreger, Esq.; Arnold & Porter LLP

(57) ABSTRACT

The present invention relates generally to Apo2L/TRAIL purification involving crystallization.

30 Claims, 4 Drawing Sheets

FOREIGN PATENT DOCUMENTS

| | | |
|---|---|---|
| WO | WO99/11791 | 3/1999 |
| WO | WO 99/36535 | 7/1999 |
| WO | WO 99/48527 | 9/1999 |
| WO | WO 00/75191 A2 | 12/2000 |
| WO | WO01/00832 | 1/2001 |
| WO | WO 01/00832 A1 | 1/2001 |
| WO | WO 0100832 A1 * | 1/2001 |
| WO | WO 02/09755 | 2/2002 |

OTHER PUBLICATIONS

Hymowitz et al., Biochemistry. Feb. 1, 2000;39(4):633-40.*
Ray et al., Proteins. Oct. 1992;14(2):300-8, Abstract only.*
Cha et al., Immunity. Aug. 1999; 11:253-261.*
Baudier et al., FEBS Lett. Nov. 8, 1982;148(2):231-4, Abstract only.*
Nelson et al., Eds. Lehninger Principles of Biochemistry. Third Ed. Worth Publishers. 2000, pp. 130-133.*
SigmaAldrich catalog, Guanadine hydrocholoride.*
Metric Conversions—277K = 4C.*
McPherson (Eur J Biochem. 1990;189:1-23).*
Armitage et al., "Molecular and Biological Characterization of a Murine Ligand for CD40", Nature, 357(6373):80-82 (1992).
Ashkenazi et al., "Safety and Antitumor Activity of Recombinant Soluble Apo2 Ligand"Journal of Clinica;l Investigation 104(2):155-162 (1999).
Banner et al., "Crystal Structure of the Soluble Human 55 KD TNF Receptor-Human TNFβComplex: Implications for TNF Receptor Activation" Cell 73:431-445 (1993).
Bodmer et al., "Cysteine 230 is Essential for the Structure and Activity of the Cytotoxic Ligand Trail", Journal of Biological Chemistry 275:20632-20637 (2000).
Brockaus et al., "Identification of Two Types of Tumor Necrosis Factor Receptors on Human Cell Lines by Monoclonal Antibodies", Proc. Natl. Acad. Sci. USA 87:3127-3131 (1990).
Browning et al., "Lymphotoxin β, a Novel Member of the TNF family that Forms a Heteromeric Complex with Lymphotoxin on the Cell Surface" Cell 72:847-856 (1993).
Chicheportiche et al., "TWEAK, A New Secreted Ligand in the Tumor Necrosis Factor Family that Weakly Induces Apoptosis", Journal of Biological Chemistry 272(51):32401-32410 (1997).
Chinnaiyan et al., "Combined Effect of Tumor Necrosis Factor-Related Apoptosis-Inducing Ligand and Ionizing Radiation in Breast Cancer Therapy", Proc. Natl. Acad. Sci. 97:1754-1759 (2000).
Darby et al., "Disulfide Bonds in Protein Folding and Stability", Methods in Enzymology, B.A. Shirley, Totowa, NJ: Human Press Inc., Chpt. 10, vol. 40:219-252 (1995).
Dealtry et al., DNA Fragmentation and Cytotoxicity cause by Tumor Necrosis Factor is Enhanced by Interferon-γEuropean Journal of Immunology 17:689-693 (1987).
Delgi-Esposti et al., "Cloning and Characterization of TRAIL-R3, a Novel member of the Emerging Trail Receptor Family", Journal of Experimental Medicine 186(7):1165-1170 (1997).
Delgi-Esposti et al., "The Novel Receptor TRAIL-R4 Induces NF-KB and Portects Against TRAIL-Mediated Apoptosis, yet Retains an Incomplete Death Domain", Immunity 7:813-820 (1997).
Gazitt, Y., "TRAIL is a potent Inducer of Apoptosis in Myeloma Cells Derived from Multiple Myeloma Patients and is not Cytotoxic to Hematopoietic Stem Cells", Leukemia 13:1817-1824 (1998).
Gliniak et al., "Tumor Necrosis Factor-Related Apoptosis-Inducing Ligand's Antitumor Activity in Vivo is Enhanced by the Chemoptherapeutic Agent CPT-11", Cancer Research 59:6153-6158 (1999).
Goodwin et al., "Molecular Cloning and Expression of the Type 1 and Type 2 Murine Receptors for Tumor Necrosis Factor", Mol. Cell. Bio. 11:3020-3026 (1991).
Griffith et al., "Monocyte-mediated Tumoricidial Activity Via the Tumor Necrosis Factor_related Cytokine, TRAIL", Journal of Experimental Medicine 189:1343-1353.
Gruss et al., "Tumor Necrosis Factor Ligand Superfamily: Involvement in the Pathology of Malignant Lymphomas", Blood 85:3378-3404.

Hahne et al., "APRIL, A New Ligand of the Tumor Necrosis Factor Family, Stimulates Tumor Cell Growth", Journal of Experimental Medicine 188(6):1185-1190 (1998).
Hale et al., "Demostration of In Vitro and In Vivo Efficacy of Two Biologically Active Human Soluble TNF Receptors Expressed in *E. coli*", J. Cell Biochem (abstract only, supple. 15F, p. 424) pp. 113 (1991).
Hohman et al., "Two Different Cell Types Have Different Major Receptors for Human Necrosis Factor (TNFα)" Journal of Biological Chemistry 264:14927-14934 (1998).
Hymowitz et al., "A unique Zinc-Binding Site Revealed by the High-Resolution X-Ray Structure of Homotrimeric Apo2L/TRAIL" Biochemistry 39(4):633-640 (2000).
Hyymowitz et al., "Triggering Cell Death: The Crystal Structure of Apo2L/TRAIL in a Complex with Death Receptor 5", Molecular Cell 4(4):563-571 (1999).
Itoh et al., "The Polypeptide Encoded by the cDNA for Human Cell Surface Antigen Fas can Mediate Apoptosis", cell 66:233-243 (1991).
Jeremias et al., "TRAIL/Apo-2-Ligand-Induced Apoptosis in Human T Cells", European Journal of Immunology 28:143-152 (1998).
Jo et al., "Apoptosis Induced in Normal Human Hepatocytes by Tumor Necrosis Factor-related Apoptosis-Inducing Ligand", Nature Medicine 6(5):564-567 (2000).
Johnson et al., "Regulation of Apo-2 Ligand/TRAIL Expression in NK Cells-Involvement in NK Cell-Mediated Cytotoxicity", Cytokine 11:664-672 (1999).
Johnson et al., "Expression and Structure of the Human NGF Receptor" Cell 47:545-554 (1986).
Katsikis et al., "Interleukin-1β Converting Enzyme-like Protease Involvement in FAS-Induced Peripheral Blood T Cell Apoptosis in HIV Infection. TNF-Related Apoptosis-Inducing Ligand can Mediate Activation-Induced T Cell Death in HIV Infection", Journal of Experimental Medicine.
Keane, et al., "Chemotherapy Augments TRAIL-Induced Apoptosis in Breast Cell Lines", Cancer Research 59:734-741(1999).
Kohno et al., "A Second Tumor Necrosis Factor Receptor Gene Product can Shed a Naturally Occuring Tumor Necrosis Factor Inhibitor", Proc. Natl. Acad. Sci. USA 87:8331-8335 (1990).
Lawrence et al., "Differential Hepatocyte Toxicity of Recombinant Apo2l/TRAIL Versions", Nature Medicine 7(4):383-385 (2001).
Lweis et al., "Cloning and Expression of cNDAs for Two Distinct Murine Tumor Necrosis Factor Receptors Demostrates One Receptor is Species Specific", PNAS USA 88:2830-2834 (1991).
Loetscher et al., "Molecular Cloning and Expression of the HUman 55 kd Tumor Necrosis Factor Receptor", Cell 61:351-359 (1990).
MacFarlane et al., "Identification and Molecular Cloning of Two Novel Receptors for the Cytotoxic Ligand TRAIL" Journal of Biological Chemistry 272(41):25417-25420 (1997).
Mallet et al., "Characterization of the MRC OX40 Antigen of Activated CD4 Positive T Lymphocytes—A Molecule Related to Nerve Growth Factor Receptor", EMBO Journal 9(4):1063-1068 (1990).
Mariani et al., "Interleukin 1β-Converting Enzyme Related Proteases/Caspases are Involved in Trail-Induced Apoptosis of Myeloma and Leukemia Cells", Journal of Cell Biology 137:221-229 (1997).
Marsters et al.,"A Novel Receptor for Apow2L/TRAIL Contains a Truncated Death Domain" Current Biology 7:1003-1006 (1997).
Marsters et al., "Identification of a Ligand for the Death-Domain-Containing Receptor Apo3", Current Biology 8(9):525-528 (1998).
Miura et al., Critical Contribution of Tumor Necrosis Factor-Related Apoptosis-Inducing Ligand (Trail) to Apoptosis of Human CD4 T Cells in Hiv-1 -Infected Hu-PBL-NOD-SCID Mice:, Journal of Experimental Medicine 193:651-660 (2001).
Mizutani et al., Synergistic Cytotoxicity and Apoptosis by Apo-2 Ligand and Adriamycin Against Bladder Cancer Cells:, Clin. Cancer Res. 5:2605-2612 (1999).
Mongkolsapaya et al., "Cutting Edge: Lymphocyte Inhibitor of TRAIL (TNF-Related Apoptosis-Inducing Ligand): A New Receptor Protecting Lymphocytes from the Death Ligand TRAIL", J. Immunol. 160(1):3-6 (1998).
Moore et al., "BLyS: Member of the Tumor Necrosis Factor Family and B Lymphocyte Stimulator", Science 285(5425):260-263 (1999).

Mukhopadhyay et al., "Identification and Characterization of a Novel Cytokine, THANK, a TNF Homologue that Activates Apoptosis, Nuclear Factor-KB, and c-Jun NH$_2$-Terminal Kinase", J. Bio. Chem. 274:15978-15981 (1999).

Nagata, S., "Steering Anti-Cancer Drugs Way from the TRAIL" Nature Medicine 6(5):502-503 (2000).

Nophar et al., "soluble Froms of Tumor Necrosis Factor Receptors (TNF-Rs). The cDNA for the Type 1 TNF-R, Cloned Using Amino Acid Sequence Data of its Soluble Form, Encodes Both the Cell Surface and a Soluble Form of the Receptor", EMBO Journal. 9:3269-3278 (1990).

Pan et al., An Antagonist Decoy Receptor and a Death-Domain Containing Receptor for TRAIL, Science 277:815-818 (1997).

Pan et al., "The Receptor for the Cytotoxic Ligand TRAIL", Science 276:111-113 (1997).

Pan et al., "TRUNDD, A New Member of the Trail Receptor Family that Antagonizes TRAIL Signalling", FEBS Letters 424(1-2):41-45 (1998).

Pitti et al., "Genomic Amplification of a Decoy Receptor for FAS Ligand inLung and Colon Cancer", Nature 396(6712):699-703 (1998).

Pitti et al., "Induction of Apoptosis by Apop-2 Ligand, a NEW Member of the Tumor Necrosis Factor Cytokine Family", Journal of Biological Chemistry 271:12687-12690 (1996).

Qin et al., "Avoiding Premature Apoptosis of Normal Epidermanl Cells", Nature Madecine 7(4):385-386 (2001).

Radeke et al., "Gene Transfer Molecular Cloning of the Rat Nerve Growth Factor Receptor", Nature 325:593-597 (1987).

Rieger et al., APO2 Ligand: A Novel Lethal Weapon Against Malignant Glioma? FEBS Letters 427:124-128 (1998).

Roth et al., "Locoregional Apo2L/TRAIL Eradicates Intracranial Human Malignant Giloma Xenografts in Athymic Mice in the Absense of Neurotoxicity", Biochem. Biophys. Res. Comm. 265:479-483 (1999).

Schall et al., "Molecular Cloning and Expression of a Receptor for Human Necrosis Factor", Cell 61:361-370 (1990).

Schmid et al., "DNA Fragmentation: Manifestation of Target Cell Destruct. Mediated by Cytotoxic T-Cell Lines, Lymphotoxin-Secreating Helper-T-Cell Clones, and Cell_free Lymphtoxin-in-Containing Supernatant", PNAS, USA 83:1881-1885 (1986).

Schneider et al., "BAFF, A Novel Ligand of the Tumor Necrosis Factor Family, Stimulates B Cell Growth", Journal of Experimental Medicine 189:1747-1756 (1999).

Schneider et al., "Characterization of Two Receptors for TRAIL" FEBS Letters 416:329-334 (1997).

Screaton et al., "TRICK2, A New Alternatively Spliced Receptor that Transduces the Cytotoxic Signal From TRAIL" Current Biology 7:693:696 (1997).

Sheridan et al., "Control of TRAIL-Induced Apoptosis by a Family of Signaling and Decoy Receptors" Science 277:818-821 (1997).

Shu et al., "TALL-1 is a Novel Member of the TNF Family that is Down-Regulated by Mitogens", J. Leukocyte Biol. 65:680-683 (1999).

Smith et al., "A Receptor for Tumor Necrosis Factor Defines an Unusual Family of Cellular and Viral Proteins" Science 248:1019-1023 (1990).

Smith et al., "T2 Open Reading Frame from the Shope Fibroma Virus Encodes a Soluble Form of the TNF Receptor", Biochem. & Biophys. Res. Comm. 176:335-342 (1991).

Song et al., "Tumor Necrosis Factor-Related Apoptosis-Inducing Ligand (TRAIL) is an Inhibitor of Autoimmune Inflammation and Cell Cycle Progression", Journal of Experimental Medicine 191(7):1095-1103 (2000).

Stamenkovic et al., "A B-Lymphocyte Activation Molecule Related to the Nerve Growth Factor Receptor and Induced by Cytokines in Carcinomas", EMBO Jounral 8(5):1403-1410 (1989).

Thomas et al., "TNF-Related Apoptosis-Inducing Ligand (TRAIL) Induces Apoptosis in Fas Ligand-Resistant Melanoma Cells and Mediates CD4 T cell Killing of Target Cells" J. Immunol. 161:2195-2200 (1998).

Upton et al., "Myxoma Virus Expresses a Secreted Protein with Homology to the Tumor Necrosis Factor Receptor Gene Family that Contributes to Viral Virulence", Virology 184:370-382 (1991).

Upton et al., "Tumorigenic Poxviruses: genomic Organization and DNA Sequence of the Telomeric Region of the Shope Fibroma Virus Geome" Virology 160:20-30 (1987).

Wlaczak et al., "TRAIL-R2: A Novel Apoptosis-Mediating Receptor for TRAII" EMBO Journal 16(17):5386-5397(1997).

*Walczak et al., "Tumoricidal Activity of Tumor Necrosis Factor-related Apoptosis-Inducing Ligand in Vivo" Nature Med. 5:157-163.

Wiley et al., "Identification and Characterization of a New Member of the TNF Family that Induces Apoptosis" Immunity 3:673-682 (1995).

Wu et al., "KILLER/DR5 is a DNA Damge-Inducible p53-Regulated Death Receptor Gene", Nature Genetics 17:141-143 (1997).

Yu et al., "Tumor Necrosis Factor-Related Apoptosis-Inducing Ligand-mediated Apoptosis in Androgen-Independent Prostate Cancer Cells" cancer Research 60:2384-2389 (2000).

Hymowitz et al., Biochemisty, Jan. 4, 2000;39:633-640.

Walczak et al., Nature Medicine, Feb. 1999 5(2):157-163.

Ashkenzi et al., J. Clin. Invest., Jul. 1999; 104(2):155-162.

Craft et al., Clin. chem., Jan. 1988;34(1):44-48 Abstract Only.

Meyer et al., Pharm. Biotechol. 2002;13:85-107, Abstract Only.

Information Hyperlink Over Proteins [IHOP]-TNFSF10.

Page et al., J. Pharm. Pharmacol., Jan. 2000;52(1):19-26, Abstract Only.

Cha et al., "2.8 A Resolution Crystal Structure of Human TRAIL, A Cytokine with Selective Antitumor Activity" Immunity, Cell Press, US. vol. 11, No. 2, Aug. 1999, pp. 253-261 XP002236164 ISSN: 1074-7613.

Rowlett, Roger S., "Protein X-Ray Crystallography Methods", 2$^{nd}$ Edition (Jun. 2005).

* cited by examiner

```
  1  TTTCCTCACTGACTATAAAGAATAGAAGGAAGGGCTTCAGTGACCGGCTGCCTGCTGACTTACAGCAGTCAGACTCTGACAGGATC

1  ATGGCTATGATGGAGTCCAGGGTGTACTTACCAAGGAGTCAGGAGCTGAAGCAGATGCAGGAGACAGTACTCCAAAGTGGCATTGCTTGTTTCTTAAAGAA
  1  MetAlaMetMetGluValGlnGlyGlyProSerLeuGlyIleGlnThrCysValLeuIleValIlePheThrValLeuLeuGlnSerLeuCys

181  GTGGCTGTAACTTACGTGTACTTTACCAAGGAGTCAGGAGCTGAAGCAGATGCAGGAGACAGTACTCCAAAGTGGCATTGCTTGTTTCTTAAAGAA
 31  ValAlaValThrTyrValTyrPheThrAsnGluLeuLysGlnMetGlnLeuLysSerGlyIleAlaCysPyeLeuL6sGlu

271  GATGACAGTTATTGGGACCCAATGACGAAGAGAGTATGAACAGCCCCTGCTGGCAAGTCCGTCAGCTCGTTAGAAAG
 61  AspAspSerTyrTrpAspProAsnAspGluGluSerMetAsnSerProCysTrpGlnValLysTrpGlnLeuArgGlnLeuValArgLys

361  ATGATTTTGAGAACCTCTGAGGAAACCATTTCTACAGTTCAAGAAAAGCAACAAAATATTTCTCCCCTAGTGAGAGAAAGAGGTCCNCAG
 91  MetIleLeuArgThrSerGluGlnThrIleSerThrValGlnGluLysGlnAsnIleSerProLeuValArgGluArgGlyProGln
                                                *

451  AGAGTAGCAGCTCACATAACTGGGACCCAGAGGAAGCAACACATTGTCTCTTCCAAACTCCAAGAATGAAAAGGCTCTGGGCCGCAAA
121  ArgValAlaAlaHisIleThrGlyThrArgGlyArgSerAsnThrLeuSerSerProAsnSerLysAsnGluLysAlaLeuGlyArgLys

541  ATAAACTCCTGGAATCATCAAGGAGTGGGCATTCTGAGCAACTGCACTTGAGGAATGGTGAACTGGTCATCCATGAAAAGGG
151  IleAsnSerTrpGluSerSerArgSerGlyHisSerPheLeuSerAsnLeuHisLeuArgAsnGlyValLeuValIleHisGluLysGly

631  TTTTACTACTACTATTCCAAACATATTTCGATTTCAAGGAGAAATAAAAGTGCTAGAAATAGTGTTGGTCTAAAGATGCAGAATATGGACTCTAT
181  PheTyrTyrIleTyrSerGlnThrTyrPheArgPheGlnIleAsnMetValGlnTyrIle

721  TACAAATACACAAGTTATCCTGACCCTATATTGTTGATGAAAAGTGCTAGAAATAGTGTTGGTCTAAAGATGCAGAATATGGACTCTAT
211  TyrLysTyrSerTyrProAspIleLeuLeuMetLysSerAlaArgAsnSerCysTrpSerLysAspAlaGluTyrGlyLeuTyr

811  TCCATCTATCAAGGGGAATATTTGAGCTTAAGGAAAATGACAGAATTTTTGTTCTGTAACAAATGAGCACTTGATAGACATGGACCAT
241  SerIleTyrGlnGlyGlyIlePheGluLeuLysGluAsnAspArgIlePheValSerValThrAsnGluHisLeuIleAspMetAspHis

901  GAAGCCAGTTTTTCGGGCCTTTTCAAGACTGCTAACTGACCTGAAAAGCAATAACCTCAAAGTGACTATTCAGTTTTCAGGAT
271  GluAlaSerPhePheGlyAlaPheLeuValGlyStp

991  GATACACTATGAAGATGTTTCAAAAATCTGACCAAAACAAAACAGAAA
```

FIG. 1

SEQUENCE LISTING

<160> NUMBER OF SEQ ID NOS: 2

<210> SEQ ID NO 1
<211> LENGTH: 281
<212> TYPE: PRT
<213> ORGANISM: Homo Sapiens

<400> SEQUENCE: 1

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu

```
                130                  135                  140
Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
            165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
            195                 200                 205

Tyr Ile Tyr Lys Tyr Thr Ser Tyr Pro Asp Pro Ile Leu Leu Met Lys
210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
            245                 250                 255

Phe Val Ser Val Thr Asn Glu His Leu Ile Asp Met Asp His Glu Ala
            260                 265                 270

Ser Phe Phe Gly Ala Phe Leu Val Gly
            275                 280

<210> SEQ ID NO 2
<211> LENGTH: 1042
<212> TYPE: DNA
<213> ORGANISM: Homo Sapiens
<220> FEATURE:
<221> NAME/KEY: unsure
<222> LOCATION: 447
<223> OTHER INFORMATION: n = T or G

<400> SEQUENCE: 2
tttcctcact gactataaaa gaatagagaa ggaagggctt cagtgaccgg ctgcctggct      60
gacttacagc agtcagactc tgacaggatc atggctatga tggaggtcca gggggggaccc    120 agcctgggac agacctgcgt gctgatcgtg atcttcacag tgctcctgca gtctctctgt    180
gtggctgtaa cttacgtgta ctttaccaac gagctgaagc agatgcagga caagtactcc    240
aaaagtggca ttgcttgttt cttaaaagaa gatgacagtt attgggaccc caatgacgaa    300
gagagtatga cagcccctg ctggcaagtc aagtggcaac tccgtcagct cgttagaaag     360
atgattttga gaacctctga ggaaaccatt tctacagttc aagaaaagca acaaaatatt    420
tctcccctag tgagagaaag aggtccncag agagtagcag ctcacataac tgggaccaga    480
ggaagaagca acacattgtc ttctccaaac tccaagaatg aaaaggctct gggccgcaaa    540
ataaactcct gggaatcatc aaggagtggg cattcattcc tgagcaactt gcacttgagg    600
aatggtgaac tggtcatcca tgaaaaaggg ttttactaca tctattccca acatactttt    660
cgatttcagg aggaaataaa agaaaacaca agaacgaca aacaaatggt ccaatatatt      720
tacaaataca caagttatcc tgaccctata ttgttgatga aagtgctag aaatagttgt      780 tggtctaaag atgcagaata tggactctat tccatctatc aagggggaat atttgagctt    840
aaggaaaatg acagaatttt tgtttctgta acaaatgagc acttgataga catggaccat    900
gaagccagtt ttttcggggc cttttagtt ggctaactga cctggaaaga aaagcaata      960 acctcaaagt gactattcag ttttcaggat gatacactat gaagatgttt caaaaatct    1020 gaccaaaaca aacaaacaga aa                                             1042
```

APO-2 LIGAND/TRAIL FORMULATIONS

RELATED APPLICATIONS

This application is continuation-in-part of U.S. patent application Ser. No. 10/771,254, filed Feb. 3, 2004, which is a continuation-in-part of international application PCT/US02/36251 (designating the US) filed Nov. 12, 2002.

FIELD OF THE INVENTION

The present invention relates generally to Apo2L/TRAIL purification involving crystallization.

BACKGROUND OF THE INVENTION

Various molecules, such as tumor necrosis factor-alpha ("TNF-alpha"), tumor necrosis factor-beta ("TNF-beta" or "lymphotoxin-alpha"), lymphotoxin-beta ("LT-beta"), CD30 ligand, CD27 ligand, CD40 ligand, OX-40 ligand, 4-1BB ligand, Apo-1 ligand (also referred to as Fas ligand or CD95 ligand), Apo-2 ligand (also referred to as Apo2L or TRAIL), Apo-3 ligand (also referred to as TWEAK), APRIL, OPG ligand (also referred to as RANK ligand, ODF, or TRANCE), and TALL-1 (also referred to as BlyS, BAFF or THANK) have been identified as members of the tumor necrosis factor ("TNF") family of cytokines [See, e.g., Gruss and Dower, *Blood*, 85:3378-3404 (1995); Schmid et al., *Proc. Natl. Acad. Sci.*, 83:1881 (1986); Dealtry et al., *Eur. J. Immunol.*, 17:689 (1987); Pitti et al., *J. Biol. Chem.*, 271:12687-12690 (1996); Wiley et al., *Immunity*, 3:673-682 (1995); Browning et al., *Cell*, 72:847-856 (1993); Armitage et al. *Nature*, 357:80-82 (1992), WO 97/01633 published Jan. 16, 1997; WO 97/25428 published Jul. 17, 1997; Marsters et al., *Curr. Biol.*, 8:525-528 (1998); Chicheportiche et al., *Biol. Chem.*, 272:32401-32410 (1997); Hahne et al., *J. Exp. Med.*, 188:1185-1190 (1998); WO98/28426 published Jul. 2, 1998; WO98/46751 published Oct. 22, 1998; WO/98/18921 published May 7, 1998; Moore et al., *Science*, 285:260-263 (1999); Shu et al., *J. Leukocyte Biol.*, 65:680 (1999); Schneider et al., *J. Exp. Med.*, 189: 1747-1756 (1999); Mukhopadhyay et al., *J. Biol. Chem.*, 274:15978-15981 (1999)]. Among these molecules, TNF-alpha, TNF-beta, CD30 ligand, 4-1BB ligand, Apo-1 ligand, Apo-2 ligand (Apo2L/TRAIL) and Apo-3 ligand (TWEAK) have been reported to be involved in apoptotic cell death.

Apo2L/TRAIL was identified several years ago as a member of the TNF family of cytokines. [see, e.g., Wiley et al., *Immunity*, 3:673-682 (1995); Pitti et al., *J. Biol. Chem.*, 271: 12697-12690 (1996)] The full-length human Apo2L/TRAIL polypeptide is a 281 amino acid long, Type II transmembrane protein. Some cells can produce a natural soluble form of the polypeptide, through enzymatic cleavage of the polypeptide's extracellular region [Mariani et al., *J. Cell. Biol.*, 137: 221-229 (1997)]. Crystallographic studies of soluble forms of Apo2L/TRAIL reveal a homotrimeric structure similar to the structures of TNF and other related proteins [Hymowitz et al., *Molec. Cell*, 4:563-571 (1999); Hymowitz et al., *Biochemistry*, 39:633-644 (2000)]. Apo2L/TRAIL, unlike other TNF family members however, was found to have a unique structural feature in that three cysteine residues (at position 230 of each subunit in the homotrimer) together coordinate a zinc atom, and that the zinc binding is important for trimer stability and biological activity. [Hymowitz et al., supra; Bodmer et al., *J. Biol. Chem.*, 275:20632-20637 (2000)]

It has been reported in the literature that Apo2L/TRAIL may play a role in immune system modulation, including autoimmune diseases such as rheumatoid arthritis, and in the treatment of HIV [see, e.g., Thomas et al., *J. Immunol.*, 161: 2195-2200 (1998); Johnsen et al., *Cytokine*, 11:664-672 (1999); Griffith et al., *J. Exp. Med.*, 189:1343-1353 (1999); Song et al., *J. Exp. Med.*, 191:1095-1103 (2000); Jeremias et al., *Eur. J. Immunol.*, 28:143-152 (1998); Katsikis et al., *J. Exp. Med.*, 186:1365-1372 (1997); Miura et al., *J. Exp. Med.*, 193:651-660 (2001)].

Soluble forms of Apo2L/TRAIL have also been reported to induce apoptosis in a variety of cancer cells in vitro, including colon, lung, breast, prostate, bladder, kidney, ovarian and brain tumors, as well as melanoma, leukemia, and multiple myeloma [see, e.g., Wiley et al., supra; Pitti et al., supra; Rieger et al., *FEBS Letters*, 427:124-128 (1998); Ashkenazi et al., *J. Clin. Invest.*, 104:155-162 (1999); Walczak et al., *Nature Med.*, 5:157-163 (1999); Keane et al., *Cancer Research*, 59:734-741 (1999); Mizutani et al., *Clin. Cancer Res.*, 5:2605-2612 (1999); Gazitt, *Leukemia*, 13:1817-1824 (1999); Yu et al., *Cancer Res.*, 60:2384-2389 (2000); Chinnaiyan et al., *Proc. Natl. Acad. Sci.*, 97:1754-1759 (2000)]. In vivo studies in murine tumor models further suggest that Apo2L/TRAIL, alone or in combination with chemotherapy or radiation therapy, can exert substantial anti-tumor effects [see, e.g., Ashkenazi et al., supra; Walzcak et al., supra; Gliniak et al., *Cancer Res.*, 59:6153-6158 (1999); Chinnaiyan et al., supra; Roth et al., *Biochem. Biophys. Res. Comm.*, 265: 1999 (1999)]. In contrast to many types of cancer cells, most normal human cell types appear to be resistant to apoptosis induction by certain recombinant forms of Apo2L/TRAIL [Ashkenazi et al., supra; Walzcak et al., supra]. Jo et al. has reported that a polyhistidine-tagged soluble form of Apo2L/TRAIL induced apoptosis in vitro in normal isolated human, but not non-human, hepatocytes [Jo et al., *Nature Med.*, 6:564-567 (2000); see also, Nagata, *Nature Med.*, 6:502-503 (2000)]. It is believed that certain recombinant Apo2L/TRAIL preparations may vary in terms of biochemical properties and biological activities on diseased versus normal cells, depending, for example, on the presence or absence of a tag molecule, zinc content, and % trimer content [See, Lawrence et al., *Nature Med., Letter to the Editor*, 7:383-385 (2001); Qin et al., *Nature Med., Letter to the Editor*, 7:385-386 (2001)].

Induction of various cellular responses mediated by such TNF family cytokines is believed to be initiated by their binding to specific cell receptors. Previously, two distinct TNF receptors of approximately 55-kDa (TNFR1) and 75-kDa (TNFR2) were identified [Hohman et al., *J. Biol. Chem.*, 264:14927-14934 (1989); Brockhaus et al., *Proc. Natl. Acad. Sci.*, 87:3127-3131 (1990); EP 417,563, published Mar. 20, 1991; Loetscher et al., *Cell*, 61:351 (1990); Schall et al., *Cell*, 61:361 (1990); Smith et al., *Science*, 248: 1019-1023 (1990); Lewis et al., *Proc. Natl. Acad. Sci.*, 88:2830-2834 (1991); Goodwin et al., *Mol. Cell. Biol.*, 11:3020-3026 (1991)]. Those TNFRs were found to share the typical structure of cell surface receptors including extracellular, transmembrane and intracellular regions. The extracellular portions of both receptors were found naturally also as soluble TNF-binding proteins [Nophar, Y. et al., *EMBO J.*, 9:3269 (1990); and Kohno, T. et al., *Proc. Natl. Acad. Sci. U.S.A.*, 87:8331 (1990); Hale et al., *J. Cell. Biochem. Supplement* 15F, 1991, p. 113 (P424)].

The extracellular portion of type 1 and type 2 TNFRs (TNFR1 and TNFR2) contains a repetitive amino acid sequence pattern of four cysteine-rich domains (CRDs) designated 1 through 4, starting from the NH$_2$-terminus. [Schall et al., supra; Loetscher et al., supra; Smith et al., supra; Nophar et al., supra; Kohno et al., supra; Banner et al., *Cell*, 73:431-435 (1993)]. A similar repetitive pattern of CRDs exists in several other cell-surface proteins, including the p75 nerve growth factor receptor (NGFR) [Johnson et al., *Cell*, 47:545 (1986); Radeke et al., *Nature*, 325:593 (1987)], the B cell antigen CD40 [Stamenkovic et al., *EMBO J.*, 8:1403 (1989)], the T cell antigen OX40 [Mallet et al., *EMBO J.*, 9:1063 (1990)] and the Fas antigen [Yonehara et al., supra and Itoh et al., *Cell*, 66:233-243 (1991)]. CRDs are also found in the soluble TNFR (sTNFR)-like T2 proteins of the Shope and myxoma poxviruses [Upton et al., *Virology*, 160:20-29 (1987); Smith et al., *Biochem. Biophys. Res. Commun.*, 176: 335 (1991); Upton et al., *Virology*, 184:370 (1991)]. Optimal alignment of these sequences indicates that the positions of the cysteine residues are well conserved. These receptors are sometimes collectively referred to as members of the TNF/NGF receptor superfamily.

The TNF family ligands identified to date, with the exception of lymphotoxin-beta, are typically type II transmembrane proteins, whose C-terminus is extracellular. In contrast, most receptors in the TNF receptor (TNFR) family identified to date are typically type I transmembrane proteins. In both the TNF ligand and receptor families, however, homology identified between family members has been found mainly in the extracellular domain ("ECD"). Several of the TNF family cytokines, including TNF-alpha, Apo-1 ligand and CD40 ligand, are cleaved proteolytically at the cell surface; the resulting protein in each case typically forms a homotrimeric molecule that functions as a soluble cytokine. TNF receptor family proteins are also usually cleaved proteolytically to release soluble receptor ECDs that can function as inhibitors of the cognate cytokines.

Pan et al. have disclosed another TNF receptor family member referred to as "DR4" [Pan et al., *Science*, 276:111-113 (1997); see also WO98/32856 published Jul. 30, 1998]. The DR4 was reported to contain a cytoplasmic death domain capable of engaging the cell suicide apparatus. Pan et al. disclose that DR4 is believed to be a receptor for the ligand known as Apo2L/TRAIL.

In Sheridan et al., *Science*, 277:818-821 (1997) and Pan et al., *Science*, 277:815-818 (1997), another molecule believed to be a receptor for Apo2L/TRAIL is described [see also, WO98/51793 published Nov. 19, 1998; WO98/41629 published Sep. 24, 1998]. That molecule is referred to as DR5 (it has also been alternatively referred to as Apo-2; TRAIL-R, TR6, Tango-63, hAPO8, TRICK2 or KILLER [Screaton et al., *Curr. Biol.*, 7:693-696 (1997); Walczak et al., *EMBO J.*, 16:5386-5387 (1997); Wu et al., *Nature Genetics*, 17:141-143 (1997); WO98/35986 published Aug. 20, 1998; EP870,827 published Oct. 14, 1998; WO98/46643 published Oct. 22, 1998; WO99/02653 published Jan. 21, 1999; WO99/09165 published Feb. 25, 1999; WO99/11791 published Mar. 11, 1999]. Like DR4, DR5 is reported to contain a cytoplasmic death domain and be capable of signaling apoptosis. The crystal structure of the complex formed between Apo-2L/TRAIL and DR5 is described in Hymowitz et al., *Molecular Cell*, 4:563-571 (1999).

A further group of recently identified receptors are referred to as "decoy receptors," which are believed to function as inhibitors, rather than transducers of signaling. This group includes DCR1 (also referred to as TRID, LIT or TRAIL-R3) [Pan et al., *Science*, 276:111-113 (1997); Sheridan et al., *Science*, 277:818-821 (1997); McFarlane et al., *J. Biol. Chem.*, 272:25417-25420 (1997); Schneider et al., *FEBS Letters*, 416:329-334 (1997); Degli-Esposti et al., *J. Exp. Med.*, 186:1165-1170 (1997); and Mongkolsapaya et al., *J. Immunol.*, 160:3-6 (1998)] and DCR2 (also called TRUNDD or TRAIL-R4) [Marsters et al., *Curr. Biol.*, 7:1003-1006 (1997); Pan et al., *FEBS Letters*, 424:41-45 (1998); Degli-Esposti et al., *Immunity*, 7:813-820 (1997)], both cell surface molecules, as well as OPG [Simonet et al., supra; Emery et al., infra] and DCR3 [Pitti et al., *Nature*, 396:699-703 (1998)], both of which are secreted, soluble proteins. Apo2L/TRAIL has been reported to bind those receptors referred to as DcR1, DcR2 and OPG.

Apo2L/TRAIL is believed to act through the cell surface "death receptors" DR4 and DR5 to activate caspases, or enzymes that carry out the cell death program. Upon ligand binding, both DR4 and DR5 can trigger apoptosis independently by recruiting and activating the apoptosis initiator, caspase-8, through the death-domain-containing adaptor molecule referred to as FADD/Mort1 [Kischkel et al., *Immunity*, 12:611-620 (2000); Sprick et al., *Immunity*, 12:599-609 (2000); Bodmer et al., *Nature Cell Biol.*, 2:241-243 (2000)]. In contrast to DR4 and DR5, the DcR1 and DcR2 receptors do not signal apoptosis.

For a review of the TNF family of cytokines and their receptors, see Ashkenazi and Dixit, *Science*, 281:1305-1308 (1998); Ashkenazi and Dixit, *Curr. Opin. Cell Biol.*, 11:255-260 (2000); Golstein, *Curr. Biol.*, 7:750-753 (1997); Gruss and Dower, supra; Nagata, *Cell*, 88:355-365 (1997); Locksley et al., *Cell*, 104:487-501 (2001).

SUMMARY OF THE INVENTION

Certain proteins, such as Apo2L/TRAIL and other members of the TNF family of cytokines, exhibit biological activity when the protein is in a trimer or trimeric form. Thus, for purposes of therapeutic or even diagnostic use, formulations of such proteins are desired wherein the protein is stable and remains biologically active, particularly stable in a trimeric form.

Applicants surprisingly found that the unique molecular structure of APO2L/TRAIL, under certain conditions, allows it to spontaneously crystallize. This property enabled the development of an efficient and scaleable recovery/purification process for APO2L/TRAIL that utilizes crystallization as a purification step. In addition, the experience obtained with APO2L/TRAIL allowed the development of a recovery and purification process involving crystallization that can be used to proteins capable of crystallization in general.

In one aspect, the present invention relates to a method of recovering Apo2L/TRAIL from a mixture comprising
(a) loading the mixture on a cation exchange column;
(b) washing the cation exchange column with an equilibration buffer whereby non-binding components present in the mixture are removed;
(c) eluting Apo2L/TRAIL bound to the cation exchange column with an elution buffer;
(d) gradually cooling the eluate to a temperature of about 2 to 4° C., whereby Apo2L/TRAIL is spontaneously precipitated in a crystalline form to yield a mixture of mother liquor and Apo2L/TRAIL crystals; and
(e) recovering Apo2L/TRAIL from the mixture obtained in step (d) in a purity of at least about 99%.

In a particular embodiment, the mixture loaded on the cation exchange column is a culture medium or cell lysate of Apo2L/TRAIL producing cells.

In another embodiment, the mixture is the cell lysate of Apo2L/TRAIL producing *E. coli* host cells.

In yet another embodiment, the lysate is clarified prior to loading on the cation exchange column.

In a further embodiment, the eluate obtained in step (c) is subjected to the crystallization step of (d) without additional purification.

The cation exchange column may, for example, be an SP-Sepharose column.

In a still further embodiment, pH of the mixture loaded on the cation exchange column (e.g. SP-Sepharose) is or is adjusted to about 7.5. The elution of Apo2L/TRAIL may, for example, be performed in an elution buffer comprising 100-200 mM NaCl or 100-150 mM $Na_2SO_4$ in a buffer adjusting the pH to 7.5-7.8.

In further embodiments, in step (d) the eluate is cooled from a temperature of about 15 to 30° C. to a temperature of about 2 to 8° C. in about 1 to 60 hours, or to a temperature of about 2 to 8° C. in about 1 to 8 hours, or to a temperature of about 2 to 8° C. in about 1 hour, or to a temperature of about 4° C. in about 1 hour.

In yet another embodiment, the pH of the eluate is or is adjusted to pH 7.0-8.0, such as pH 7.3, prior to crystallization.

In another embodiment, the pH of the eluate is or is adjusted to about 7.5-8.0 after crystallization.

In an additional embodiment, in step (d) the temperature of about 2 to 4° C. is maintained until equilibrium solubility of Apo2L/TRAIL is achieved or nearly achieved.

In the course of performing the method of the invention, in step (d), solubility of Apo2L/TRAIl may be decreased by the addition of an anti-solvent, such as, for example, polyethylene glycol (PEG), MPD, ethanol, isopropanol, and/or dioxane.

Thus, for example, PEG having a molecular weight of the PEG between about 400 and about 10,000 daltons is used as an anti-solvent. In other representative embodiments, the molecular weight of PEG is 400, 3,350 or 10,000 daltons.

In a further embodiment, in step (e) Apo2L/TRAIL is recovered in the form of crystals separated from the mother liquor by filtration or centrifugation or a combination thereof. The pH of the mother liquor may be adjusted to about 8.0 prior to filtration to decrease solubility.

In a further aspect, the recovery/purification method of the present invention further comprises the steps of dissolving the Apo2L/TRAIL crystals obtained in step (d) of the above-described method, and subjecting the solution obtained to a second chromatographic purification step In one embodiment, the second chromatographic purification step is hydrophobic interaction chromatography, which may, for example, be performed on a Phenyl-Sepharose column.

In another embodiment, the second chromatographic purification step is cation exchange chromatography performed, for example, on an CM-Sepharose or SP-Sepharose column.

In a further embodiment, Apo2L/TRAIL is recovered and formulated following the second chromatographic purification step by ultrafiltration-diafiltration.

In additional embodiments, the purity of the purified protein is at least about 99.5%, or at least about 99.9%

BRIEF DESCRIPTION OF THE DRAWINGS

FIG. 1 shows the nucleotide sequence of human Apo-2L/TRAIL cDNA (SEQ ID NO:2) and its derived amino acid sequence (SEQ ID NO:1). The "N" at nucleotide position 447 (in SEQ ID NO:2) is used to indicate the nucleotide base may be a "T" or "G".

DETAILED DESCRIPTION OF THE INVENTION

A. Definitions

Figure 2:
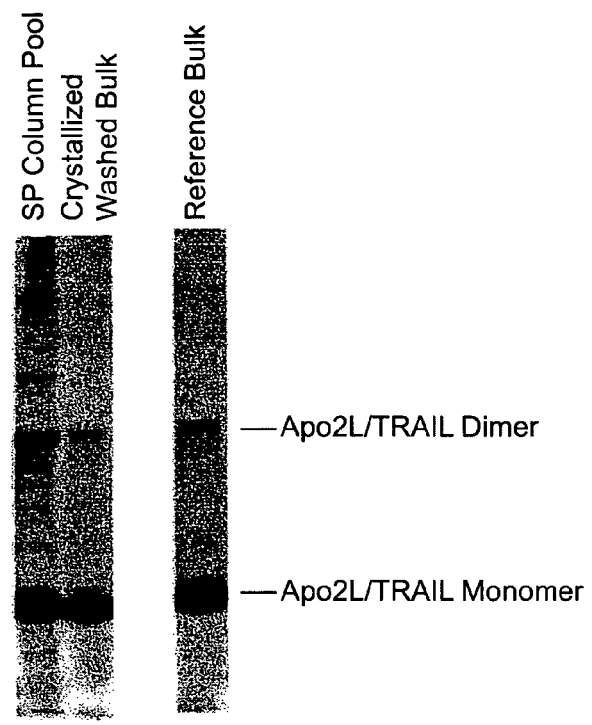
FIG. 2 shows a SDS-PAGE silver stain gel illustrating purity of the described Apo2L/TRAIL preparations.

"TNF family member" is used in a broad sense to refer to various polypeptides that share some similarity to tumor necrosis factor (TNF) with respect to structure or function. Certain structural and functional characteristics associated with the TNF family of polypeptides are known in the art and described, for example, in the above Background of the Invention. Such polypeptides include but are not limited to those polypeptides referred to in the art as TNF-alpha, TNF-beta, CD40 ligand, CD30 ligand, CD27 ligand, OX-40 ligand, 4-1BB ligand, Apo-1 ligand (also referred to as Fas ligand or CD95 ligand), Apo-2L/TRAIL (also referred to as TRAIL), Apo-3 ligand (also referred to as TWEAK), APRIL, OPG ligand (also referred to as RANK ligand, ODF, or TRANCE), and TALL-1 (also referred to as BlyS, BAFF or THANK) (See, e.g., Gruss and Dower, Blood 1995, 85:3378-3404; Pitti et al., J. Biol. Chem. 1996, 271:12687-12690; Wiley et al., Immunity 1995, 3:673-682; Browning et al., Cell 1993, 72:847-856; Armitage et al. Nature 1992, 357:80-82, PCT Publication Nos. WO 97/01633; and WO 97/25428; Marsters et al., Curr. Biol. 1998, 8:525-528; Chicheportiche et al., Biol. Chem. 1997, 272:32401-32410; Hahne et al., J. Exp. Med. 1998, 188:1185-1190; PCT Publication Nos. WO98/28426; WO98/46751; and WO/98/18921; Moore et al., Science 1999, 285:260-263; Shu et al., J. Leukocyte Biol. 1999, 65:680; Schneider et al., J. Exp. Med. 1999, 189:1747-1756; Mukhopadhyay et al., J. Biol. Chem. 1999, 274:15978-15981).

The terms "Apo2L/TRAIL", "Apo2L", "Apo-2 ligand" and "TRAIL" are used herein to refer to a polypeptide sequence which includes amino acid residues 114-281, inclusive, 95-281, inclusive, residues 92-281, inclusive, residues 91-281, inclusive, residues 41-281, inclusive, residues 15-281, inclusive, or residues 1-281, inclusive, of the amino acid sequence shown in FIG. 1 (SEQ ID NO:1), as well as biologically active fragments, deletional, insertional, or substitutional variants of the above sequences. In one embodiment, the polypeptide sequence comprises residues 114-281 of FIG. 1 (SEQ ID NO:1), and optionally, consists of residues 114-281 of FIG. 1 (SEQ ID NO:1). Optionally, the polypeptide sequence comprises residues 92-281 or residues 91-281 of FIG. 1 (SEQ ID NO:1). The Apo-2L polypeptides may be encoded by the native nucleotide sequence shown in FIG. 1 (SEQ ID NO:2). Optionally, the codon which encodes residue Pro119 (FIG. 1; SEQ ID NO:2) may be "CCT" or "CCG". In other embodiments, the fragments or variants are biologically active and have at least about 80% amino acid sequence identity, more preferably at least about 90% sequence identity, and even more preferably, at least 95%, 96%, 97%, 98%, or 99% sequence identity with any one of the above recited Apo2L/TRAIL sequences. Optionally, the Apo2L/TRAIL polypeptide is encoded by a nucleotide sequence which hybridizes under stringent conditions with the encoding polynucleotide sequence provided in FIG. 1 (SEQ ID NO:2). The definition encompasses substitutional variants of Apo2L/TRAIL in which at least one of its native amino acids are substituted by an alanine residue. Particular substitutional variants of the Apo2L/TRAIL include those in which at least one amino acid is substituted by an alanine residue. These substitutional variants include those identified, for example, as "D203A"; "D218A" and "D269A." This nomenclature is used to identify Apo2L/TRAIL variants wherein the aspartic acid residues at positions 203, 218, and/or 269 (using the numbering shown in FIG. 1 (SEQ ID NO:1)) are substituted by alanine residues. Optionally, the Apo2L variants may comprise one or more of the alanine substitutions which are recited in Table I of published PCT application WO 01/00832. Substitutional variants include one or more of the residue substitutions identified in Table I of WO 01/00832 published Jan. 4, 2001. The definition also encompasses a native sequence Apo2L/TRAIL isolated from an Apo2L/TRAIL source or prepared by recombinant or synthetic methods. The Apo2L/TRAIL of the invention includes the polypeptides referred to as Apo2L/TRAIL or TRAIL disclosed in PCT Publication Nos. WO97/01633 and WO97/25428. The terms "Apo2L/TRAIL" or "Apo2L" are used to refer generally to forms of the Apo2L/TRAIL which include monomer, dimer or trimer forms of the polypeptide. All numbering of amino acid residues referred to in the Apo2L sequence use the numbering according to FIG. 1 (SEQ ID NO:1), unless specifically stated otherwise. For instance, "D203" or "Asp203" refers to the aspartic acid residue at position 203 in the sequence provided in FIG. 1 (SEQ ID NO:1).

The term "Apo2L/TRAIL extracellular domain" or "Apo2L/TRAIL ECD" refers to a form of Apo2L/TRAIL which is essentially free of transmembrane and cytoplasmic domains. Ordinarily, the ECD will have less than 1% of such transmembrane and cytoplasmic domains, and preferably, will have less than 0.5% of such domains. It will be understood that any transmembrane domain(s) identified for the polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified. In preferred embodiments, the ECD will consist of a soluble, extracellular domain sequence of the polypeptide which is free of the transmembrane and cytoplasmic or intracellular domains (and is not membrane bound). Particular extracellular domain sequences of Apo-2L/TRAIL are described in PCT Publication Nos. WO97/01633 and WO97/25428.

The term "Apo2L/TRAIL monomer" or "Apo2L monomer" refers to a covalent chain of an extracellular domain sequence of Apo2L.

The term "Apo2L/TRAIL dimer" or "Apo2L dimer" refers to two Apo-2L monomers joined in a covalent linkage via a disulfide bond. The term as used herein includes free standing Apo2L dimers and Apo2L dimers that are within trimeric forms of Apo2L (i.e., associated with another, third Apo2L monomer).

The term "Ap92L/TRAIL trimer" or "Apo2L trimer" refers to three Apo2L monomers that are non-covalently associated.

The term "Apo2L/TRAIL aggregate" is used to refer to self-associated higher oligomeric forms of Apo2L/TRAIL, such as Apo2L/TRAIL trimers, which form, for instance, hexameric and nanomeric forms of Apo2L/TRAIL.

Determination of the presence and quantity of Apo2L/TRAIL monomer, dimer, or trimer (or other aggregates) may be made using methods and assays known in the art (and using commercially available materials), such as native size exclusion HPLC ("SEC"), denaturing size exclusion using sodium dodecyl sulphate ("SDS-SEC"), reverse phase HPLC, capillary electrophoresis, and including those methods described in further detail in the Examples below.

The term "tagged" when used herein refers to a chimeric polypeptide comprising Apo2L/TRAIL, or a portion thereof, fused to a "tag polypeptide". The tag polypeptide has enough residues to provide an epitope against which an antibody can be made or to provide some other function, such as metal ion chelation, yet is short enough such that it generally does not interfere with activity of the TNF family cytokine. The tag polypeptide preferably also is fairly unique so that a tag-specific antibody does not substantially cross-react with other epitopes. Suitable tag polypeptides generally have at least six amino acid residues and usually between about 8 to about 50 amino acid residues (preferably, between about 10 to about 20 residues).

The term "divalent metal ion" refers to a metal ion having two positive charges. Examples of divalent metal ions include but are not limited to zinc, cobalt, nickel, cadmium, magnesium, and manganese. Particular forms of such metals that may be employed include salt forms (e.g., pharmaceutically acceptable salt forms), such as chloride, acetate, carbonate, citrate and sulfate forms of the above mentioned divalent metal ions. Optionally, a divalent metal ion for use in the present invention is zinc, and preferably, the salt form, zinc sulfate or zinc chloride.

"Isolated," when used to describe the various proteins disclosed herein, means protein that has been identified and separated and/or recovered from a component of its natural environment. Contaminant components of its natural environment are materials that would typically interfere with diagnostic or therapeutic uses for the protein, and may include enzymes, hormones, and other proteinaceous or non-proteinaceous solutes. In preferred embodiments, the protein will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain, or (3) to homogeneity by mass spectroscopic or peptide mapping techniques. Isolated protein includes protein in situ within recombinant cells, since at least one component of the Apo2L/TRAIL natural environment will not be present. Ordinarily, however, isolated protein will be prepared by at least one purification step.

An "isolated" Apo2L/TRAIL nucleic acid molecule is a nucleic acid molecule that is identified and separated from at least one contaminant nucleic acid molecule with which it is ordinarily associated in the natural source of the Apo2L/TRAIL nucleic acid. An isolated Apo2L/TRAIL nucleic acid molecule is other than in the form or setting in which it is found in nature. Isolated Apo2L/TRAIL nucleic acid molecules therefore are distinguished from the Apo2L/TRAIL nucleic acid molecule as it exists in natural cells. However, an isolated Apo2L/TRAIL nucleic acid molecule includes Apo2L/TRAIL nucleic acid molecules contained in cells that ordinarily express Apo2L/TRAIL where, for example, the nucleic acid molecule is in a chromosomal location different from that of natural cells.

"Percent (%) amino acid sequence identity" with respect to the sequences identified herein is defined as the percentage of amino acid residues in a candidate sequence that are identical with the amino acid residues in the Apo2L/TRAIL sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art can determine appropriate parameters for measuring alignment, including assigning algorithms needed to achieve maximal alignment over the full-length sequences being compared. For purposes herein, percent amino acid identity values can be obtained using the sequence comparison computer program, ALIGN-2, which was authored by Genentech, Inc. and the source code of which has been filed with user documentation in the US Copyright Office, Washington, DC, 20559, registered under the U.S. Copyright Registration No. TXU510087. The ALIGN-2 program is publicly available through Genentech, Inc., South San Francisco, Calif. All sequence comparison parameters are set by the ALIGN-2 program and do not vary.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to re-anneal when complementary strands are present in an environment below their melting temperature. The higher the degree of desired identity between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"High stringency conditions", as defined herein, are identified by those that: (1) employ low ionic strength and high temperature for washing; 0.015 M sodium chloride/0.0015 M sodium citrate/0.1% sodium dodecyl sulfate at 50° C.; (2) employ during hybridization a denaturing agent; 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include overnight incubation at 37° C. in a solution comprising: 20% formamide, 5×SSC (150 mM NaCl, 15 mM trisodium citrate), 50 mM sodium phosphate (pH. 7.6), 5× Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "storage-stable" is used to describe a formulation having a shelf-life acceptable for a product in the distribution chain of commerce, for instance, at least 12 months at a given temperature, and preferably, at least 24 months at a given temperature. Optionally, such a storage-stable formulation contains no more than 5% aggregates, no more than 10% dimers, and/or minimal changes in charge heterogeneity or biological activity. Degradation pathways for proteins can involve chemical instability (i.e. any process which involves modification of the protein by bond formation or cleavage resulting in a new chemical entity) or physical instability (i.e. changes in the higher order structure of the protein). Chemical instability can result from, for example, deamidation, racemization, hydrolysis, oxidation, beta elimination or disulfide exchange. Physical instability can result from, for example, denaturation, aggregation, precipitation or adsorption. The three most common protein degradation pathways are protein aggregation, deamidation and oxidation. Cleland et al. *Critical Reviews in Therapeutic Drug Carrier Systems* 10(4): 307-377 (1993).

As used herein, "soluble" refers to polypeptides that, when in aqueous solutions, are completely dissolved, resulting in a clear to slightly opalescent solution with no visible particulates, as assessed by visual inspection. A further assay of the turbidity of the solution (or solubility of the protein) may be made by measuring UV absorbances at 340 nm to 360 nm with a 1 cm pathlength cell where turbidity at 20 mg/ml is less than 0.05 absorbance units.

An "osmolyte" refers to a tonicity modifier or osmotic adjuster that lends osmolality to a solution. Osmolality refers to the total osmotic activity contributed by ions and nonionized molecules to a solution. Examples include inorganic salts such as sodium chloride, polyethylene glycols (PEGs), polypropylene glycol, sugars such as sucrose or trehalose, glycerol, amino acids, and sugar alcohols such as mannitol known to the art that are generally regarded as safe (GRAS).

"Preservatives" can act to prevent bacteria, viruses, and fungi from proliferating in the formulation, and anti-oxidants, or other compounds can function in various ways to preserve the stability of the formulation. Examples include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of compounds include aromatic alcohols such as phenol and benzyl alcohol, alkyl parabens such as methyl or propyl paraben, and m-cresol. Optionally, such a compound is phenol or benzyl alcohol. The preservative or other compound will optionally be included in a liquid or aqueous form of the Apo2L/TRAIL formulation, but not usually in a lyophilized form of the formulation. In the latter case, the preservative or other compound will typically be present in the water for injection (WFI) or bacteriostatic water for injection (BWFI) used for reconstitution.

A "surfactant" can act to decrease turbidity or denaturation of a protein in a formulation. Examples of surfactants include non-ionic surfactant such as a polysorbate, e.g., polysorbates 20, 60, or 80, a poloxamer, e.g., poloxamer 184 or 188, Pluronic polyols, ethylene/propylene block polymers or any others known to the art that are GRAS. Optionally, the surfactant is a polysorbate or poloxamer.

A "buffer" as used herein is any suitable buffer that is GRAS and generally confers a pH from about 6 to about 9, optionally from about 6.5 to about 8.5, and optionally at about 7 to about 7.5, if the polypeptide is Apo2L/TRAIL. Examples include Tris, Hepes, triethanolamine, histidine, or any others known to the art to have the desired effect.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors; platelet-growth factor; transforming growth factors (TGFs) such as TGF-α and TGF-β; insulin-like growth factor-I and -II; erythropoietin (EPO); osteoinductive factors; interferons such as interferon-α, -β, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-2, IL-3, IL-4, IL-5, IL-6, IL-7, IL-8, IL-9, IL-11, IL-12; and other polypeptide factors including LIF and kit ligand (KL). As used herein, the term cytokine includes proteins from natural sources or from recombinant cell culture and biologically active equivalents of the native sequence cytokines.

The term "cytotoxic agent" as used herein refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin gammaI and calicheamicin phiI1, see, e.g., Agnew, Chem Intl. Ed. Engl., 33:183-186 (1994); dynemicin, including dynemicin A; bisphosphonates, such as clodronate; an esperamicin; as well as neocarzinostatin chromophore and related chromoprotein enediyne antiobiotic chromomophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (Adriamycin™) (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; PSK®; razoxane; rhizoxin; sizofiran; spirogermanium; tenuazonic acid; triaziquone; 2, 2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhône-Poulenc Rorer, Antony, France); chlorambucil; gemcitabine (Gemzar™); 6-thioguanine; mercaptopurine; methotrexate; platinum analogs such as cisplatin and carboplatin; vinblastine; platinum; etoposide (VP-16); ifosfamide; mitoxantrone; vincristine; vinorelbine (Navelbine™); novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above. Also included in this definition are anti-hormonal agents that act to regulate or inhibit hormone action on tumors such as anti-estrogens and selective estrogen receptor modulators (SERMs), including, for example, tamoxifen (including Nolvadex™), raloxifene, droloxifene, 4-hydroxytamoxifen, trioxifene, keoxifene, LY117018, onapristone, and toremifene (Fareston™); aromatase inhibitors that inhibit the enzyme aromatase, which regulates estrogen production in the adrenal glands, such as, for example, 4(5)-imidazoles, aminoglutethimide, megestrol acetate (Megace™), exemestane, formestane, fadrozole, vorozole (Rivisor™), letrozole (Femara™), and anastrozole (Arimidex™); and anti-androgens such as flutamide, nilutamide, bicalutamide, leuprolide, and goserelin; and pharmaceutically acceptable salts, acids or derivatives of any of the above.

A "growth inhibitory agent" when used herein refers to a compound or composition which inhibits growth of a cell, especially cancer cell overexpressing any of the genes identified herein, either in vitro or in vivo. Thus, the growth inhibitory agent is one which significantly reduces the percentage of cells overexpressing such genes in S phase. Examples of growth inhibitory agents include agents that block cell cycle progression (at a place other than S phase), such as agents that induce G1 arrest and M-phase arrest. Classical M-phase blockers include the vincas (vincristine and vinblastine), paclitaxel (TAXOL®), and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogens, and antineoplastic drugs" by Murakami et al. (W B Saunders: Philadelphia, 1995), especially p. 13.

"Biologically active" or "biological activity" for the purposes herein means (a) having the ability to induce or stimulate apoptosis in at least one type of mammalian cancer cell or virally-infected cell in vivo or ex vivo, either alone as a single agent or in combination with a chemotherapeutic agent (b) capable of raising an antibody, i.e., immunogenic; (c) capable of binding and/or stimulating a receptor for Apo2L/TRAIL (such receptors may include the DR4 receptor, DR5 receptor, OPG, DcR1 receptor, and DcR2 receptor); or (d) retaining the activity of a native or naturally-occurring Apo2L/TRAIL polypeptide. Assays for determining biological activity of the Apo2L/TRAIL can be conducted using methods known in the art, such as DNA fragmentation (see, e.g., Marsters et al., Curr. Biology, 6: 1669 (1996)), caspase inactivation, DR4 binding, DR5 binding (see, e.g., WO 98/51793, published Nov. 19, 1998), DcR1 binding (see, e.g., WO 98/58062, published Dec. 23, 1998), DcR2 binding (see, e.g., WO 99/10484, published Mar. 4, 1999) as well as the assays described in PCT Publication Nos. WO97/01633, WO97/25428, WO 01/00832, and WO 01/22987.

The terms "apoptosis" and "apoptotic activity" are used in a broad sense and refer to the orderly or controlled form of cell death in mammals that is typically accompanied by one or more characteristic cell changes, including condensation of cytoplasm, loss of plasma membrane microvilli, segmentation of the nucleus, degradation of chromosomal DNA or loss of mitochondrial function. This activity can be determined and measured, for instance, by cell viability assays (such as Alamar blue assays or MTT assays), FACS analysis, caspase activation, DNA fragmentation (see, for example, Nicoletti et al., *J. Immunol. Methods*, 139:271-279 (1991), and poly-ADP ribose polymerase, "PARP", cleavage assays known in the art.

As used herein, the term "disorder" in general refers to any condition that would benefit from treatment with the compositions described herein, including any disease or disorder that can be treated by effective amounts of polypeptides such as Apo2L/TRAIL. This includes chronic and acute disorders, as well as those pathological conditions which predispose the mammal to the disorder in question. Non-limiting examples of disorders to be treated herein include benign and malignant cancers; inflammatory, angiogenic, and immunologic disorders, autoimmune disorders, arthritis (including rheumatoid arthritis), multiple sclerosis, and HIV/AIDS.

The terms "cancer", "cancerous", or "malignant" refer to or describe the physiological condition in mammals that is typically characterized by unregulated cell growth. Examples of cancer include but are not limited to, carcinoma, lymphoma, leukemia, blastoma, and sarcoma. More particular examples of such cancers include squamous cell carcinoma, myeloma, small-cell lung cancer, non-small cell lung cancer, glioma, gastrointestinal cancer, renal cancer, ovarian cancer, liver cancer, lymphoblastic leukemia, lymphocytic leukemia, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, and head and neck cancer. Optionally, the cancer cells express DR4 and/or DR5 receptor(s).

The terms "treating", "treatment" and "therapy" as used herein refer to curative therapy, prophylactic therapy, and preventative therapy. Consecutive treatment or administration refers to treatment on at least a daily basis without interruption in treatment by one or more days. Intermittent treatment or administration, or treatment or administration in an intermittent fashion, refers to treatment that is not consecutive, but rather cyclic in nature.

The term "mammal" as used herein refers to any mammal classified as a mammal, including humans, cows, horses, dogs and cats. In a preferred embodiment of the invention, the mammal is a human.

The term "polyol" when used herein refers broadly to polyhydric alcohol compounds. Polyols can be any water-soluble poly(alkylene oxide) polymer for example, and can have a linear or branched chain. Preferred polyols include those substituted at one or more hydroxyl positions with a chemical group, such as an alkyl group having between one and four carbons. Typically, the polyol is a poly(alkylene glycol), preferably poly(ethylene glycol) (PEG). However, those skilled in the art recognize that other polyols, such as, for example, poly(propylene glycol) and polyethylene-polypropylene glycol copolymers, can be employed for conjugation to proteins and other biomolecules. Polyols include those known in the art and those publicly available, such as from commercially available sources.

B. Exemplary Methods and Materials for Carrying Out the Invention

The present invention provides methods for recovery and purification of Apo2L/TRAIL. In particular, the invention provides methods, involving crystallization, to recover and purify Apo2L/TRAIL from mixtures in which it is accompanied by other contaminants, such as contaminating proteins and other impurities. In a specific embodiment, the invention provides methods to recover and purify Apo2L/TRAIL from recombinant host cultures or cell lysates, such as cell lysates of Apo2L/TRAIL producing *E. coli* recombinant host cells.

The basis for these purification methods is the unexpected finding that Apo2L/TRAIL readily and spontaneously crystallizes in certain buffer systems. This finding allows using crystallization as an efficient purification step in the purification scheme of Apo2L/TRAIL. In particular, experimental work underlying the present invention has shown that crystallization can be implemented as a step in the purification process of APO2L/TRAIL and other proteins showing a similar tendency of spontaneous crystallization. The incorporation of a crystallization step in the purification scheme allows the reduction of purification process steps while maintaining comparable yields to traditional purification schemes using multiple chromatographic purification steps, without crystallization. Accordingly, implementing crystallization into the purification process may result in marked time and cost savings, without compromising efficiency, product yields or product quality.

B.1 Production of Apo2L/TRAIL

The description below relates to methods of producing Apo2L/TRAIL by culturing host cells transformed or transfected with a vector containing Apo2L/TRAIL encoding nucleic acid and recovering the polypeptide from the cell culture.

The DNA encoding Apo2L/TRAIL may be obtained from any cDNA library prepared from tissue believed to possess the Apo2L/TRAIL mRNA and to express it at a detectable level. Accordingly, human Apo2L/TRAIL DNA can be conveniently obtained from a cDNA library prepared from human tissues, such as the bacteriophage library of human placental cDNA as described in PCT Publication WO97/25428. The Apo2L/TRAIL-encoding gene may also be obtained from a genomic library or by oligonucleotide synthesis.

Libraries can be screened with probes (such as antibodies to the Apo2L/TRAIL or oligonucleotides of at least about 20-80 bases) designed to identify the gene of interest or the protein encoded by it. Screening the cDNA or genomic library with the selected probe may be conducted using standard procedures (Sambrook et al., *Molecular Cloning: A Laboratory Manual*; New York: Cold Spring Harbor Laboratory Press, 1989). An alternative means to isolate the gene encoding Apo2L/TRAIL is to use PCR methodology (Sambrook et al., supra; Dieffenbach et al., *PCR Primer:A Laboratory Manual*, Cold Spring Harbor Laboratory Press, 1995).

Amino acid sequence fragments or variants of Apo2L/TRAIL can be prepared by introducing appropriate nucleotide changes into the Apo2L/TRAIL DNA, or by synthesis of the desired Apo2L/TRAIL polypeptide. Such fragments or variants represent insertions, substitutions, and/or deletions of residues within or at one or both of the ends of the intracellular region, the transmembrane region, or the extracellular region, or of the amino acid sequence shown for the full-length Apo2L/TRAIL in FIG. 1 (SEQ ID NO:1). Any combination of insertion, substitution, and/or deletion can be made to arrive at the final construct, provided that the final construct possesses, for instance, a desired biological activity or apoptotic activity as defined herein. In a preferred embodiment, the fragments or variants have at least about 80% amino acid sequence identity, more preferably, at least about 90% sequence identity, and even more preferably, at least 95%, 96%, 97%, 98% or 99% sequence identity with, for example, the sequences identified herein for the intracellular, transmembrane, or extracellular domains of Apo2L/TRAIL, or the full-length sequence for Apo-2L/TRAIL. The amino acid changes also may alter post-translational processes of the Apo-2L/TRAIL, such as changing the number or position of glycosylation sites or altering the membrane anchoring characteristics.

Variations in the Apo2L/TRAIL sequence as described above can be made using any of the techniques and guidelines for conservative and non-conservative mutations set forth in U.S. Pat. No. 5,364,934. These include oligonucleotide-mediated (site-directed) mutagenesis, alanine scanning, and PCR mutagenesis.

Scanning amino acid analysis can be employed to identify one or more amino acids along a contiguous sequence. Among the preferred scanning amino acids are relatively small, neutral amino acids. Such amino acids include alanine, glycine, serine and cysteine. Alanine is typically a preferred scanning amino acid among this group because it eliminates the side-chain beyond the beta-carbon and is less likely to alter the main-chain conformation of the variant. (Cunningham et al., Science 1989, 244:1081). Alanine is also typically preferred because it is the most common amino acid. Further, it is frequently found in both buried and exposed positions (Creighton, *The Proteins*, (W. H. Freeman & Co., NY); Chothia, J. Mol. Biol. 1976, 150:1).

Particular Apo2L/TRAIL variants of the present invention include those Apo2L/TRAIL polypeptides which include one or more of the recited alanine substitutions provided in TABLE I of published PCT application WO 01/00832. Such Apo2L/TRAIL variants will typically comprise a non-naturally occurring amino acid sequence which differs from a native Apo2L/TRAIL amino acid sequence (such as provided in FIG. 1; SEQ ID NO:1, for a full length or mature form of Apo2L/TRAIL or an extracellular domain sequence thereof) in at least one or more amino acids. Optionally, the one or more amino acids which differ in the Apo2L/TRAIL variant as compared to a native Apo2L/TRAIL will comprise amino acid substitution(s) such as those indicated in Table I of WO 01/00832. Apo2L/TRAIL variants of the invention include soluble Apo2L/TRAIL variants comprising residues 91-281, 92-281, 95-281 or 114-281 of FIG. 1 (SEQ ID NO:1) and having one or more amino acid substitutions. Preferred Apo2L/TRAIL variants will include those variants comprising residues 91-281, 92-281, 95-281 or 114-281 of FIG. 1 (SEQ ID NO:1) and having one or more amino acid substitutions which enhance biological activity, such as receptor binding. A particularly preferred variant comprises residues 114-281 of FIG. 1 (SEQ ID NO:1). In a specific embodiment, Apo-2L/TRAIL consists of residues 114-281 of FIG. 1 (SEQ ID NO:1).

As described in WO 01/00832 published Jan. 4, 2001, the x-ray crystal structure of the extracellular domain of Apo2L/TRAIL identified, and alanine-scanning mutagenesis was performed to provide the mapping of its receptor contact regions. The structure obtained for Apo2L/TRAIL revealed a homotrimeric protein which contains a novel divalent metal ion (zinc) binding site that coordinates the interaction of the Apo2L/TRAIL trimer molecule's three subunits. Like other members of the TNF family, Apo2L/TRAIL appears to comprise a compact trimer formed of three jelly roll monomers which bury approximately 5100 Angstrom$^2$ (1700 Angstrom$^2$ per monomer) to form the globular trimer. The position of the core beta-strands was well conserved compared to the other structurally characterized members of the TNF family, TNF-alpha, TNF-beta, and CD40L when compared to the core strands of TNF-alpha or TNF-beta.

Variations in the Apo2L/TRAIL sequence also included within the scope of the invention relate to amino-terminal derivatives or modified forms. Such Apo2L/TRAIL sequences may include any of the Apo2L/TRAIL polypeptides described herein having a methionine or modified methionine (such as formyl methionyl or other blocked methionyl species) at the N-terminus of the polypeptide sequence.

The nucleic acid (e.g., cDNA or genomic DNA) encoding native or variant Apo2L/TRAIL may be inserted into a replicable vector for further cloning (amplification of the DNA) or for expression. Various vectors are publicly available. The vector components generally include, but are not limited to, one or more of the following: a signal sequence, an origin of replication, one or more marker genes, an enhancer element, a promoter, and a transcription termination sequence, each of which is described below. Optional signal sequences, origins of replication, marker genes, enhancer elements and transcription terminator sequences that may be employed are known in the art and described in further detail in PCT Publication WO97/25428.

Expression and cloning vectors usually contain a promoter that is recognized by the host organism and is operably linked to the Apo2L/TRAIL nucleic acid sequence. Promoters are untranslated sequences located upstream (5') to the start codon of a structural gene (generally within about 100 to 1000 bp) that control the transcription and translation of a particular nucleic acid sequence, such as the Apo2L/TRAIL nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to Apo2L/TRAIL encoding DNA by removing the promoter from the source DNA by restriction enzyme digestion and inserting the isolated promoter sequence into the vector. Both the native Apo2L/TRAIL promoter sequence and many heterologous promoters may be used to direct amplification and/or expression of the Apo2L/TRAIL DNA.

Promoters suitable for use with prokaryotic and eukaryotic hosts are known in the art, and are described in further detail in PCT Publication No. WO97/25428.

Preferred methods for the production of soluble Apo2L/TRAIL in *E. coli* employ an inducible promoter for the regulation of product expression. The use of a controllable, inducible promoter allows for culture growth to the desirable cell density before induction of product expression and accumulation of significant amounts of product which may not be well tolerated by the host.

Various inducible promoter systems (including T7 polymerase, trp and alkaline phosphatase (AP)) have been evaluated by Applicants for the expression of Apo2L/TRAIL (amino acids 114-281). The use of each of the T7 polymerase, trp and alkaline phosphatase promoters resulted in significant amounts of soluble, biologically active Apo2L/TRAIL trimer being recovered from the harvested cell paste. Another optional promoter is a glycerol-phosphate promoter system.

Construction of suitable vectors containing one or more of the above-listed components employs standard ligation techniques. Isolated plasmids or DNA fragments are cleaved, tailored, and re-ligated in the form desired to generate the plasmids required.

For analysis to confirm correct sequences in plasmids constructed, the ligation mixtures can be used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced using standard techniques known in the art. (See, e.g., Messing et al., Nucleic Acids Res. 1981, 9:309; Maxam et al., Methods in Enzymology 1980, 65:499).

Expression vectors that provide for the transient expression in mammalian cells of DNA encoding Apo2L/TRAIL may be employed. In general, transient expression involves the use of an expression vector that is able to replicate efficiently in a host cell, such that the host cell accumulates many copies of the expression vector and, in turn, synthesizes high levels of a desired polypeptide encoded by the expression vector (Sambrook et al., supra). Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of Apo2L/TRAIL that are biologically active Apo2L/TRAIL.

Other methods, vectors, and host cells suitable for adaptation to the synthesis of Apo2L/TRAIL in recombinant vertebrate cell culture are described in Gething et al., Nature 1981, 293:620-625; Mantei et al., Nature 1979, 281:40-46; EP 117,060; and EP 117,058.

Suitable host cells for cloning or expressing the DNA in the vectors herein include prokaryote, yeast, or higher eukaryote cells. Suitable prokaryotes for this purpose include but are not limited to eubacteria, such as Gram-negative or Gram-positive organisms, for example, *Enterobacteriaceae* such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published Apr. 12, 1989), *Pseudomonas* such as *P. aeruginosa*, and *Streptomyces*. Preferably, the host cell should secrete minimal amounts of proteolytic enzymes.

*E. coli* is the preferred host cell for use in the present invention. *E. coli* is particularly well suited for the expression of Apo2L/TRAIL (comprising amino acids 114-281 of FIG. 1), a polypeptide of under 20 kd in size with no glycosylation requirement. As a production host, *E. coli* can be cultured to relatively high cell density and is capable of producing relatively high levels of heterologous proteins.

In addition to prokaryotes, eukaryotic microbes such as filamentous fungi or yeast are suitable cloning or expression hosts for Apo2L/TRAIL-encoding vectors. Suitable host cells for the expression of glycosylated Apo2L/TRAIL are derived from multicellular organisms. Examples of all such host cells, including CHO cells, are described further in PCT Publication No. WO97/25428.

Host cells are transfected and preferably transformed with the above-described expression or cloning vectors for Apo2L/TRAIL production and cultured in nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described (Shaw et al., Gene 1983, 23:315 and PCT Publication No. WO 89/05859). In addition, plants may be transfected using ultrasound treatment, PCT Publication No. WO 91/00358 published Jan. 10, 1991.

For mammalian cells without such cell walls, the calcium phosphate precipitation method (Graham and van der Eb, Virology 1978, 52:456-457) may be employed. General aspects of mammalian cell host system transformations have been described in U.S. Pat. No. 4,399,216. Transformations into yeast are typically carried out according to the method of Van Solingen et al., J. Bact. 1977, 130:946 and Hsiao et al. Proc. Natl. Acad. Sci. USA 1979, 76:3829. However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al. Methods in Enzymology 1990, 185:527-537 and Mansour et al. Nature 1988, 336:348-352.

Prokaryotic cells used to produce Apo2L/TRAIL may be cultured in suitable culture media as described generally in Sambrook et al., supra. Particular forms of culture media that may be employed for culturing E. coli are described further in PCT application WO 01/00832. In a particularly preferred process, APO2L/TRAIL (comprising amino acids 114-281 of FIG. 1) produced in E. coli is fermented using a zinc supply and glycerophosphate. The fermentation titers preferably range from about 4 to about 6 g/l.

Mammalian host cells used to produce Apo2L/TRAIL may be cultured in a variety of culture media.

Examples of commercially available culture media include Ham's F10 (Sigma), Minimal Essential Medium ("MEM", Sigma), RPMI-1640 (Sigma), and Dulbecco's Modified Eagle's Medium ("DMEM", Sigma). Any such media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In general, principles, protocols, and practical techniques for maximizing the productivity of mammalian cell cultures can be found in *Mammalian Cell Biotechnology: A Practical Approach*, M. Butler, ed. (IRL Press, 1991).

Expression of the Apo2L/TRAIL may be measured in a sample directly, for example, by conventional Southern blotting, Northern blotting to quantitate the transcription of mRNA (Thomas, Proc. Natl. Acad. Sci. USA 1980, 77:5201-5205), dot blotting (DNA analysis), or in situ hybridization, using an appropriately labeled probe, based on the sequences provided herein. Various labels may be employed, most commonly radioisotopes, and particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionucleotides, fluorescers or enzymes. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like.

Antibodies useful for immunohistochemical staining and/or assay of sample fluids may be either monoclonal or polyclonal, and may be prepared in any mammal. Conveniently, the antibodies may be prepared against a native Apo2L/TRAIL polypeptide or against a synthetic peptide based on the DNA sequences provided herein or against exogenous sequence fused to Apo2L/TRAIL DNA and encoding a specific antibody epitope.

The Apo-2L polypeptide may be covalently attached (hereinafter "conjugated") to one or more chemical groups. Chemical groups suitable for use in an Apo-2L conjugate are preferably not significantly toxic or immunogenic. A variety of exemplary chemical groups that can be conjugated to polypeptides are known in the art and include for example carbohydrates, such as those carbohydrates that occur naturally on glycoproteins, polyglutamate, and non-proteinaceous polymers, such as polyols (see, e.g., U.S. Pat. No. 6,245,901).

A polyol, for example, can be conjugated to polypeptides such as an Apo-2L at one or more amino acid residues, including lysine residues, as is disclosed in WO 93/00109, supra. The polyol employed can be any water-soluble poly(alkylene oxide) polymer and can have a linear or branched chain. Suitable polyols include those substituted at one or more hydroxyl positions with a chemical group, such as an alkyl group having between one and four carbons. Typically, the polyol is a poly(alkylene glycol), such as poly(ethylene glycol) (PEG), and thus, for ease of description, the remainder of the discussion relates to an exemplary embodiment wherein the polyol employed is PEG and the process of conjugating the polyol to a polypeptide is termed "pegylation." However, those skilled in the art recognize that other polyols, such as, for example, poly(propylene glycol) and polyethylene-polypropylene glycol copolymers, can be employed using the techniques for conjugation described herein for PEG.

The average molecular weight of the PEG employed in the pegylation of the Apo-2L can vary, and typically may range from about 500 to about 30,000 daltons (D). Preferably, the average molecular weight of the PEG is from about 1,000 to about 25,000 D, and more preferably from about 1,000 to about 5,000 D. In one embodiment, pegylation is carried out with PEG having an average molecular weight of about 1,000 D. Optionally, the PEG homopolymer is unsubstituted, but it may also be substituted at one end with an alkyl group. Preferably, the alkyl group is a C1-C4 alkyl group, and most preferably a methyl group. PEG preparations are commercially available, and typically, those PEG preparations suitable for use in the present invention are nonhomogeneous preparations sold according to average molecular weight. Optionally, an Apo-2L trimer will be pegylated in a manner such that a PEG molecule is linked or conjugated to one, two or each of the three monomers that make up the trimeric Apo-2L. In such an embodiment, it is preferred that the PEG employed have an average molecular weight of about 1,000 to about 5,000 D. It is also contemplated that the Apo-2L trimers may be "partially" pegylated, i.e., wherein only one or two of the three monomers that make up the trimer are linked or conjugated to PEG.

A variety of methods for pegylating proteins are known in the art. Specific methods of producing proteins conjugated to PEG include the methods described in U.S. Pat. No. 4,179, 337, U.S. Pat. No. 4,935,465 and U.S. Pat. No. 5,849,535. Typically the protein is covalently bonded via one or more of the amino acid residues of the protein to a terminal reactive group on the polymer, depending mainly on the reaction conditions, the molecular weight of the polymer, etc. The polymer with the reactive group(s) is designated herein as activated polymer. The reactive group selectively reacts with free amino or other reactive groups on the protein. The PEG polymer can be coupled to the amino or other reactive group on the protein in either a random or a site specific manner.

B.2 Crystallization of Apo2L/TRAIL

Crystallization is widely used for purification of small molecules. However, generally, crystallization techniques have not been widely applied for proteins as various parameters may affect the protein crystallization, including, for example, solubility, nucleation and growth rate, and crystal size distribution (each being a function of further parameters, such as solubility, temperature, pH, buffer, impurities, and the like). Since proteins are generally more difficult to crystallize than small molecules, the recovery and purification of therapeutic proteins to date has rarely involved a crystallization step(s).

Applicants surprisingly found that the solid state of Apo2L/TRAIL protein at 5° C. is crystalline at moderate to low ionic strength conditions, unlike many other proteins known in the art that are soluble or form amorphous precipitates under similar conditions. Further, it was found that the solid state of the Apo2L/TRAIL crystals reversibly solubilizes when brought to ambient temperature (i.e., room temperature) without a loss in protein biological activity or adverse effect on the biochemical properties of the protein. This observation was quite different from the denaturation or irreversible precipitation observed for other proteins known in the art.

Optionally, the Apo2L/TRAIL crystals are prepared by cooling a super-saturated solution of Apo-2L/TRAIL protein from about 20 to about 30° C. to below about 15° C., preferably about 2 to 8° C., more preferably, below about 2-8° C., even more preferably below about 4° C., most preferably to about 2 to 4° C. Optionally, the Apo2L/TRAIL concentration can be above 3 g/L in order to initiate spontaneous crystallization. Antisolvents can be used to initiate spontaneous crystallization at lower protein concentrations. Crystallization can be carried out in batch or semi-batch mode at a large range of scale, from a few milliliters to hundreds of liters of solution. The crystallization rate can be controlled by programmed cooling and agitation. The equipment may include, but is not limited to, agitated or static tanks with surface and/or internal temperature control. Internal baffles and draft tubes may also be used to enhance mixing in agitated tanks. Crystal nucleation can also be controlled by seeding [Moore, AIChE Practical Engineering Perspectives, Distillation and Other Industrial Separations, pp. 239-245]. The degree of super-saturation, salt composition, cooling rate, agitation rate, and seeding, among other parameters, can affect crystal formation rate, crystal size distribution, and crystal yield.

Optionally, to prepare the crystals, the solution of Apo-2L/TRAIL protein contains sodium sulphate or sodium chloride. Optionally, the salt concentration is about 100 mM to about 200 mM and optionally the pH is about 6 to about 9 (preferably, pH of about 6.5 to about 8.5).

B.3 Use of Crystallization in the Recovery and Purification of APO2L/TRAIL

In the methods of the present invention, crystallization is a step in the recovery and purification of Apo2L/TRAIL, and optionally is a step in a one-column or a two-column scheme for the recovery and purification of Apo2L/TRAIL.

In a particular embodiment, Apo2L/TRAIL is purified from a recombinant host culture or cell lysate, or clarified cell lysate using a purification process including a crystallization step. If Apo2L/TRAIL is produced in $E.\ coli$, typically the whole cell broth is harvested and homogenized to break open the $E.\ coli$ cells and release soluble Apo2L/TRAIL within the cytoplasm. After removing the solid debris, e.g. by centrifugation, the mixture is loaded onto a cation exchange chromatographic resin, such as, for example, SP-Sepharose Fast Flow or CM-Sepharose Fast Flow (Amersham Pharmacia, Sweden). Typical protocols for purifying Apo2L/TRAIL from cell broth obtained by fermentation of $E.\ coli$ are provided in Examples 2 and 3.

In a typical protocol, the pH of the whole cell broth obtained by fermentation of the $E.\ coli$ cells is adjusted to about 7.5, e.g. by addition of sodium HEPES or any other appropriate buffer. Preferably, a reducing agent, such as 1,4-dithio-threitol (DTT) or P-mercaptoethanol is added, to prevent the formation of disulfide bonds between the non-covalently bound monomers of Apo2L/TRAIL. The cells are burst open by one or more passes on a commercially available high pressure homogenizer, the cell debris is removed, and the cell lysate is clarified. Specific treatment parameters, such as selection and concentration of reagents, depend on the composition of the starting whole cell broth, such as, for example, cell density.

The Apo2L/TRAIL-containing mixture, such as a clarified cell lysate, is then loaded on a first chromatographic column, using a cation exchange resin. Cation exchange chromatography retains biomolecules by the interaction of charged groups that are acidic in nature on the surface of the resin with histidine, lysine and arginine. Cation exchange resins are commercially available from the product lines of various manufacturers, such as, for example, Sigma Aldrich. Cation exchangers include resins carrying, for example, carboxymethyl functional groups (weak cation exchanger, such as, CM cellulose/Sephadex) or sulfonic acid functional groups (strong cation exchanger, such as, SP Sephadex). In the first chromatographic purification step of the methods of the present invention, strong cation exchange columns, e.g. SP-Sepharose®, Spectra/Gel® strong cation exchangers, etc. TSKgel strong cation exchangers, etc. are preferred. In the case of an SP-Sepharose® column, the cross-linked agarose matrix with negatively charged functional groups binds to Apo2L/TRAIL while allowing the majority of the impurities and Apo2L/TRAIL variants to pass through the column. Elution can be performed using salt gradient elution or step elution, step elution being preferred since it provides better conditions for the subsequent crystallization step, without compromising yields. The elution buffer usually contains sodium chloride or sodium sulfate, and salt concentration is selected to meet the demands of the cation exchange column and the subsequent crystallization step. The SP-Sepharose® column needs a fairly high salt concentration to remove the bound Apo2L/TRAIL protein, while for the subsequent crystallization step relatively low salt concentrations are preferred, in order to lower protein solubility. Typically, about 100-150 mM $Na_2SO_4$ or 100-200 mM NaCl concentrations are used. A typical elution buffer consists of 200 mM NaCl, 50 mM HEPES, 0.05% Triton X-100, 1 mM DTT, pH 7.5.

The concentration of Apo2L/TRAIL in the cation exchange, e.g. SP-Sepharose® elution pool, influences the theoretical yield for the following crystallization step. Concentration must be high enough to maximize the solubility differences at lower temperatures, but not too high to trigger spontaneous crystallization at or around room temperature.

In a representative protocol, two wash steps are employed between loading and eluting the Apo2L/TRAIL protein. The first wash uses equilibration buffer, and the second is a salt wash, using a buffer identical to the subsequent elution buffer, except using a lower salt concentration (e.g. 100 mM NaCl instead of 200 mM NaCl).

The SP elution step, including the two wash steps, typically produces Apo2L/TRAIL concentrations around 3-6 g/L, such as about 5 g/L with yields around 80-90%. The salt wash step results in loss of the active protein, therefore, removing this step, the yield can be increased over 95%. However, elimination of this step also decreases the column's ability to remove endotoxins and extracellular proteins, thereby lowering purity.

The elution pool leaving the cation exchange column is subjected to crystallization directly without any further additional purification step, but optionally including sterile filtration. Crystallization is typically performed by gradually decreasing the temperature from about 15-30° C. to about 2 to 8° C. in a time frame that can extend as long as 60 hours, but typically is shorter, such as, for example, about 1 to 8 hours.

In a typical crystallization process, the elution pool leaving the cation exchange column is transferred into a temperature-controlled tank with adequate agitation. It is important to ensure that the vessel and protein solution are free from any particulates prior to crystallization, in order to avoid nucleation based on such solid particulates, which would influence the crystallization kinetics. For small scale applications, for example, a 1 or 2 liter Applikon® reaction vessel can be used. In the 1 L vessel, temperature is controlled via cooling coils immersed into the vessel. The 2 L reaction vessel contains a heat exchange jacket. A linear temperature ramp can be produced in both vessels by using a programmable heat exchange bath (e.g. PolyScience Programmable Temperature Circulator Model 1157). The vessel is usually equipped by an agitator to thoroughly mix the solution, and suspend the crystals once formed. The agitation rate is typically around 250 rpm for 0.4 L scale and is scaled for larger pools by keeping a constant power to volume ratio, proportional to $N^3/V$ (constant diameter agitator).

It has been found that the solubility of Apo2L/TRAIL increases with increasing salt concentration, and Apo2L/TRAIL is approximately equally soluble in sodium sulfate and sodium chloride. Crystals formed in sodium chloride have a more exaggerated thickness compared to crystals formed in sodium sulfate, which are more flat in appearance. As a result, crystals produced in sodium chloride are easier to separate by filtration, which makes sodium chloride the preferred salt. As background buffers, HEPES and TRIS typically provide comparable results.

Apo2L/TRAIL solubility decreases with increasing pH within a range of about pH 7.0 and 8.0. Higher pH tends to increase yields but can make the crystals more amorphous in appearance. In addition, the crystals are larger at higher pH, but also more fragile. In view of these considerations, a preferred pH, producing desired crystal morphology is 7.3±0.1.

The temperature ramp used during crystallization (typically from about ambient temperature to about 2° C.) had no significant effect on average crystal size or size distribution between about 1 and 24 hours. The temperature ramp may be linear, but non-linear cooling rate may also be used to further improve the crystal size profile by maintaining a constant supersaturation level as the crystallization progresses. Since Apo2L/TRAIL does not spontaneously crystallize in the buffers systems of the present invention until the temperature is below about 8° C., preferably below about 5° C., it is possible to quickly drop the temperature to around 10° C. and then slowly cool the pool to allow for crystallization.

Crystal size is influenced by the rate of agitation. By testing three different agitation rates (100 rpm, 175 rpm and 250 rpm), crystallization was found to be fastest with the greatest agitations rate, but crystal size distribution and the appearance of crystals were very similar for the 175 rpm and 250 rpm agitation rates. At lower rates, crystals are not completely suspended, and crystal aggregation may take place. At higher agitation rates care must be taken not to damage the soluble protein by exposure to shear effects at the air/liquid interface.

Crystallization efficiency may be improved by lowering the solubility of Apo2L/TRAIL. Thus, the overall yield of the crystallization step is controlled in part by the solubility of Apo2L/TRAIL in the chilled pool collected from the first cation exchange chromatography column. The two factors that affect yield are in initial concentration of Apo2L/TRAIL in the elution pool collected from the first cation exchange chromatography column (e.g. SP column), and the concentration of soluble Apo2L/TRAIL in the crystal slurry (i.e. the amount of Apo2L/TRAIL that does not crystallize). Apo2L/TRAIL which is still in solution following crystallization will be lost during filtration. The addition of anti-solvents can change the solution chemistry to lower the equilibrium solubility:

Percent theoretical yield=$[Apo2L]_{22C}-[Apo2L]_{4C}/[aPO2l]_{22C} \times 100\%$, where the subscripted numbers indicate temperature values.

By reducing the Apo2L/TRAIL in solution, less protein is removed when the mother liquor is filtered off. Anti-solvents, also known as precipitating agents, are well known in the art and can work in a variety of ways. Some anti-solvents dehydrate the solution by absorbing water. This essentially reduces the activity of water available to dissolve the protein (see, e.g. McPherson, A., 1998, Crystallization of Biological Macromolecules. Cold Spring Harbor Laboratory Press. Plainview N.Y.).

A widely used anti-solvent is polyethylene glycol (PEG), a polymer available in a wide range of molecular weight. As shown in the Examples, in the methods of the present invention PEG of higher molecular weight (3350 and 10000) provided better results. Other polymers that can be used as anti-solvents include, for example, Eudragit RS, ethylcellulose, isopropyl alcohol, ethanol, dioxane, and 2-methyl-2,4-pentanediol (MPD).

When crystallization is complete, the Apo2L/TRAIL crystals are removed, for example by filtration. The crystals may be kept suspended throughout filtration, using a built-in agitator, or can be deposited in a packed bed. It is important to avoid the formation of a compressed crystal cake, which could make it difficult to achieve the desired flow rate. Therefore, differential pressures across the packed bed must be minimized. Flow rates may vary, and typically are between about 200 cm/hr and about 100 cm/hr. The flow rate may depend on the equipment used, and the applied differential pressure during filtration. Filtration may be performed batch-wise or continuously. Further purification can be achieved, for example, by washing the deposited crystal bed with a solution that does not substantially dissolve Apo2L/TRAIL crystals, such as a chilled solution (2-8 C.) of low molarity TRIS at about pH 7.5.

Following crystallization and separation, the Apo2L/TRAIL crystals can be dissolved and stored or converted into a formulation suitable for the intended use.

Alternatively, a further chromatography purification step can be added to further improve purity by removing the anti-solvent (PEG) residues and buffer components, and reduce the levels of residual extracellular proteins, endotoxin, dimers, and aggregates. The second chromatographic column, used following crystallization, can be a cation exchange column, or a hydrophobic interaction column. Since the crystallization pool is very pure, it is typically not necessary to use a bind-and-elute mode of separation (such as typically used with SP-Sepharose or CM-Sepharose), a flow-through column, such as Phenyl Sepharose HIC resin, will typically show a good performance. The use of both types of resins, cation exchange in a bind-and-elute mode and HIC in flow-through mode, have been tested and the results are discussed in the Examples. It was found that while a bind and step elution chromatography step provides a very powerful tool for initial purification, in the second chromatography purification step, hydrophobic interaction chromatography on Phenyl-Sepharose is sufficient to provide the desired purity and yields. Since this is a flow-through step, it provides excellent yields and reduces the number of solutions required to complete the operation compared to bind and elute chromatography.

B.4 Use of Apo2L/TRAIL

The methods of the present invention provide an effective, efficient, and cost saving alternative to, for instance, purification protocols requiring multiple column purifications. As discussed above, in one embodiment, the purification scheme of the present invention involves the use of a single cation exchange column, followed by crystallization. The Apo2L/TRAIL crystals obtained by the method of the present invention can be dried for storage. Drying the crystalline material can also substantially reduce storage volume, and provide an effective way of bulk storage which avoids freezing the purified material at low concentration in formulation solution. The crystal slurry at very high protein concentration can be frozen in smaller volume containers.

In another embodiment, the Apo2L/TRAIL crystals are collected, and washed with buffer (or water) (preferably a cold buffer at a temperature of about 2 to 8° C.). The washed crystals can be re-suspended or re-dissolved at ambient temperature. Re-solubilized Apo2L/TRAIL can be further purified by hydrophobic interaction chromatography or a second step of cation exchange chromatography as described above, recrystallized, washed and stored as wet crystalline bulk material. Alternatively, the hydrophobic interaction or other chromatography step may be omitted in favor of simply recrystallizing.

The wet crystalline bulk material can be stored at −20° C. or dried for storage at ambient temperature (room temperature) or at 2-8° C. Preferably, the dried crystalline material is re-solubilized in an arginine succinate-containing formulation. Optionally, such a formulation can be sterile filtered and/or filled in individual dosage vials, and lyophilized for later reconstitution or suspension. Optionally, the dried crystalline formulation can be filled as a powder in vials and made into a solution or suspension. It may be desirable to achieve a water content of about 5% to about 10% in the dried Apo2L/TRAIL crystals.

The Apo2L/TRAIL formulations can be employed in a variety of therapeutic and non-therapeutic applications. Among these applications are methods of treating disorders, such as cancer, immune related conditions, or viral conditions. Such therapeutic and non-therapeutic applications are further described, for instance, in WO97/25428, WO97/01633, and WO 01/22987.

In the methods of the invention for treating a disorder using a formulation disclosed herein, the formulation of Apo2L/TRAIL can be directly administered to the mammal by any suitable technique, including infusion or injection. The specific route of administration will depend, e.g., on the medical history of the patient, including any perceived or anticipated side effects using Apo2L/TRAIL and the particular disorder to be corrected. Examples of parenteral administration include subcutaneous, intramuscular, intravenous, intraarterial, and intraperitoneal administration of the composition. The formulations are preferably administered as repeated intravenous (i.v.), subcutaneous (s.c.), intramuscular (i.m.) injections or infusions, intracranial infusions or as aerosol formulations suitable for intranasal or intrapulmonary delivery (for intrapulmonary delivery see, e.g., EP 257,956).

It is noted that osmotic pressure of injections may be important in subcutaneous and intramuscular injection. Injectable solutions, when hypotonic or hypertonic, may cause pain to a patient upon infusion. Usually, for the therapeutic, injectable formulations herein, it is preferred that the relative osmolarity of the injectable solution be about 300 mosm to about 600 mosm.

Apo2L/TRAIL can also be administered in the form of sustained-release preparations. Suitable examples of sustained-release preparations include semipermeable matrices of solid hydrophobic polymers containing the protein, which matrices are in the form of shaped articles, e.g., films, or microcapsules. Examples of sustained-release matrices include cellulose derivatives (e.g., carboxymethylcellulose), sucrose-acetate isobutyrate (SABER™) in non-aqueous media, polyesters, hydrogels (e.g., poly(2-hydroxyethyl-methacrylate) (Langer et al., J. Biomed. Mater. Res. 1981, 15: 167-277; Langer, Chem. Tech. 1982, 12: 98-105 or poly (vinylalcohol)), polylactides (U.S. Pat. No. 3,773,919, EP 58,481), copolymers of L-glutamic acid and gamma ethyl-L-glutamate (Sidman et al., Biopolymers 1983, 22: 547-556), non-degradable ethylene-vinyl acetate (Langer et al., supra), degradable lactic acid-glycolic acid copolymers such as the Lupron Depot (injectable microspheres composed of lactic acid-glycolic acid copolymer and leuprolide acetate), and poly-D-(−)-3-hydroxybutyric acid (EP 133,988).

One optional method of delivery for systemic-acting drugs involves administration by continuous infusion (using, e.g., slow-release devices or minipumps such as osmotic pumps or skin patches), or by injection (using, e.g., intravenous or subcutaneous means, including single-bolus administration).

The composition to be used in the therapy will be formulated and dosed in a fashion consistent with good medical practice, taking into account the clinical condition of the individual patient, the site of delivery of the composition, the method of administration, the scheduling of administration, and other factors known to practitioners. The "effective amounts" of each component for purposes herein are thus determined by such considerations and are amounts that result in bioavailability of the Apo2L/TRAIL or other drugs to the mammal.

As a general proposition, the total pharmaceutically effective amount of the Apo2L/TRAIL polypeptides administered will be in the range of from about 1 mg/kg/day to about 20 mg/kg/day based on kg of patient body weight although, as noted above, this will be subject to therapeutic discretion.

Although injection is preferred, an infusion device may also be employed for continuous infusions. An intravenous bag solution may also be employed.

It is contemplated that yet additional therapies may be employed in the methods. The one or more other therapies may include but are not limited to, administration of radiation therapy, cytokine(s), growth inhibitory agent(s), chemotherapeutic agent(s), cytotoxic agent(s), tyrosine kinase inhibitors, ras farnesyl transferase inhibitors, angiogenesis inhibitors, and cyclin-dependent kinase inhibitors which are known in the art and defined further with particularity in Section I above. In addition, therapies based on therapeutic antibodies that target tumor antigens such as Rituxan™ or Herceptin™ as well as anti-angiogenic antibodies such as anti-VEGF, or antibodies that target Apo2L receptors, such as DR5 or DR4.

Preparation and dosing schedules for chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

It may be desirable to also administer antibodies against other antigens, such as antibodies which bind to CD20, CD11a, CD18, CD40, ErbB2, EGFR, ErbB3, ErbB4, vascular endothelial factor (VEGF), or other TNFR family members (such as DR4, DR5, OPG, TNFR1, TNFR2). Alternatively, or in addition, two or more antibodies binding the same or two or more different antigens disclosed herein may be co-administered to the patient. Sometimes, it may be beneficial to also administer one or more cytokines to the patient. In one embodiment, the Apo2L formulations are co-administered with a growth inhibitory agent.

The Apo2L/TRAIL formulation may be administered concurrently or sequentially with such other agents. For example, the Apo2L/TRAIL formulation or a chemotherapeutic agent may be administered as a pre-treatment (prior to administration of any such other agents), such as a pre-treatment of cancer cells which may otherwise be resistant to the apoptotic effects of Apo2L/TRAIL.

The invention also provides kits which include a formulation described herein. A typical kit will comprise a container, preferably a vial, for Apo2L/TRAIL in one or more excipients as described above; and instructions, such as a product insert or label, directing the user as to how to employ the Apo2L/TRAIL formulation. This would preferably provide a pharmaceutical formulation. Preferably, the pharmaceutical formulation is for treating cancer or an immune related condition. Suitable containers include, for example, bottles, vials, syringes, and test tubes. The containers may be formed from a variety of materials such as glass or plastic. The container holds an Apo2L/TRAIL formulation that is effective for diagnosing or treating the disorder and may have a sterile access port (for example, the container may be an intravenous solution bag or a vial having a stopper pierceable by a hypodermic injection needle). The label on, or associated with, the container indicates that the formulation is used for diagnosing or treating the disorder of choice. The article of manufacture may further comprise a second container comprising water-for-injection, a pharmaceutically-acceptable solution, saline, Ringer's solution, or dextrose solution. It may further include other materials desirable from a commercial and user standpoint, including other buffers, diluents, filters, needles, syringes, and package inserts with instructions for use.

All patents, patent applications, publications, product descriptions, and protocols are cited throughout this application, the disclosures of which are incorporated herein by reference in their entireties.

EXAMPLES

The following examples are offered for illustrative purposes only, and are not intended to limit the scope of the present invention in any way. Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Production of Apo2L/TRAIL in E. coli and Purification by Multiple Chromatographic Steps (Without Crystallization)

A. Apo2L/TRAIL protein consisting of amino acids 114-281 (see FIG. 1) was expressed in E. coli under the AP promoter control (preparation and expression described in Example 8 (Section A) of WO 01/00832 published Jan. 4, 2001), and purified from the E. coli cell lysates by three chromatographic steps consisting of cation exchange, hydroxyapatite, and hydrophobic interaction chromatography (WO 01/00832, Example 8, Section C). In the third chromatographic separation, the Apo2L/TRAIL protein was eluted in 600 mM Na sulfate or 400 mM ammonium sulfate, 50 mM Tris, pH 7.5.

B. Another method for purification of Apo2L/TRAIL consisted of four chromatography step and two ultrafiltration/diafiltration (UFDF) steps. The whole cell broth obtained from the E. coli production process was homogenized to break open the E. coli cells and release the soluble APO2L/TRAIL held within the cytoplasm. The solid cell debris was then removed by centrifugation.

Primary isolation was performed by binding and gradient elution on a cation exchange (CEX) column (SP-Sepharose Fast Flow column). The eluate was then transferred to a hydroxyapatite (HA) chromatography column, followed by hydrophobic interaction (Phenyl-Sepharose) chromatography. After an ultrafiltration/diafiltration (UFDF) step, the mixture was loaded onto a CM-Sepharose Fast Flow column, and the eluted protein concentrated by a final UFDF step.

Example 2

Apo2L/TRAIL Crystallization as a Method of Recovery and Purification Following One-Column Purification The propensity of crystallization of Apo2L/TRAIL in Na sulfate solutions was used as a means of purifying the Apo2L/TRAIL protein from E. coli extracts. The following protocol was employed for recovery and purification of recombinant Apo2L/TRAIL without adverse effect on protein quality.

The harvested whole cell broth derived from E. coli (described in Example 1) was adjusted to pH 7.5 with 1.5 M Hepes (or 1.5M Tris) and then homogenized in a homogenizer (Gaulin corporation, Everett, Mass.) at 6,500 psi. The homogenate was diluted one to one with 5M DTT in pure water. Once the solution reaches room temperature, 5% polyethyleneimine (PEI) was added to give a final concentration of 0.1%, and the solution was flocculated for 1-2 hours. The flocculated material was centrifuged by a BTPX205 (Alfa Laval Separation AB, Sweden) continuous feed centrifuge and clarified by depth filtration. The clarified cell lysate (extract) was conditioned with Triton-X100 to a final concentration of 0.05%. The conditioned, clarified cell lysate was then loaded onto a cation exchange column (SP-Sepharose FF cation exchange resin, Amersham Pharmacia, Sweden) equilibrated in 50 mM Hepes (or 50 mM Tris)/0.05% Triton-X 100/1 mM DTT, pH 7.5. Apo2L/TRAIL bound to the column while the non-binding proteins flowed through the column and were removed by washing with equilibration buffer until absorbance at 280 nm reached baseline. The column was then washed with 3 column volumes of 0.1 M NaCl in equilibration buffer. The Apo2L/TRAIL was step-eluted using 0.1 M NaCl (or 0.1M Na$_2$SO$_4$) in 50 mM each of Hepes, Tris and Triethanolamine, 0.05% Triton-X 100 and 1 mM DTT buffer, pH 7.8.

Protein quality was assessed by SEC, SDS-SEC, IEX, and bioactivity according to methods described in Example 1.

The purity and quality of Apo2L/TRAIL recovered using the above crystallization method at a 60 L fermentation scale is shown in Table 1. For comparison, a reference standard purified by a three-chromatographic step method as described in Example 1 is also shown.

TABLE 1

| Apo2L/ TRAIL Prep. | Protein Purity | | | Protein Quality | | Bioactivity % of | |
|---|---|---|---|---|---|---|---|
| | ECP (ppm) | LAL (EU/mg) | SDS-PAGE | % Trimer by SEC | % Monomer by SDS-SEC | control (±20%) | % IEX main peak |
| Apo2L/ TRAIL purified by crystallization | 10 | 0.034 | No band at 10kDa | 99.0 | 99.0 | 126 | 63 |
| Reference material purified by standard chromatography | 0.82 | 0.023 | Band at ~10kDa | 98.9 | 98.9 | 86 | 61 |

The ambient temperature Apo2L/TRAIL pool collected from the SP column was placed in a stainless steel tank with an insulated jacket for heating and cooling. The tank was outfitted with a conical bottom and a flush bottom valve for maximal recovery of crystallized protein. The pool was agitated using a marine type impeller under modest mixing conditions. A temperature control skid was used to linearly ramp the temperature from approximately 25° C. to approximately 4° C. over the course of 1 hour. Spontaneous crystallization was observed within minutes after the pool reached 4° C. After more than 12 hours under these conditions, crystallization was complete as equilibrium solubility was nearly established. The crystals were then captured on a filtration assembly containing a 20 µm polypropylene frit. Following crystal deposition on the filter surface, the crystals were washed with chilled 20-50mM Tris at pH 7.5. An equal volume of wash buffer compared to the Apo2L/TRAIL SP pool volume was then used to remove residual mother liquor (supernatant) from the deposited crystals. Following the wash, the crystals were dissolved in 100 mM sodium sulfate/20 mM Tris at pH 7.5 by recirculating the dissolution buffer through the crystal bed at approximately 30° C. Dissolution of the crystals was observed within approximately 4 hours. The dissolved, purified Apo2L/TRAIL was then sterile filtered into a container and stored frozen at −70° C.

The purity of the Apo2L/TRAIL preparations was determined by the total *E. coli* protein (ECP) ELISA assays, Limulus Amebocyte Lysate (LAL) assay, and SDS-PAGE silver stain. ECP ELISA was performed by immobilizing affinity-purified goat anti-whole ECP antibodies on microtiter plate wells, incubating samples and then horseradish peroxidase-conjugated ECPs. The peroxidase enzymatic activity was then quantified with o-phenylenediamine by reading absorbance at 490 nm in a microtiter plate reader. Endotoxin level was determined using the Limulus Amebocyte clot lysis assay. SDS-PAGE silver stain was performed on a 10 to 20% gradient polyacrylamide gel (Daiichi Pure Chemicals) in Tris-glycine buffer containing 0.1% SDS. Electrophoresis was conducted at 50 mA constant current until dye front reached near the bottom of the gel. Gels were fixed and stained by Coomassie Brilliant Blue or Merrill silver stain methods.

Figure 3:
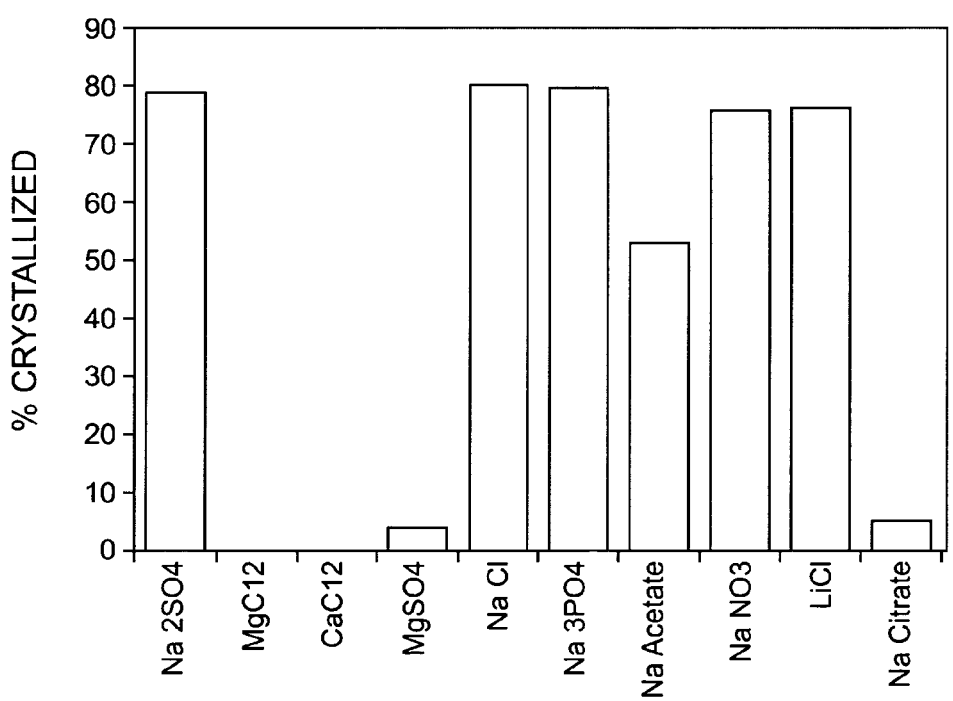
FIG. 3 shows the effects of various salts on crystallization of Apo2L/TRAIL.

As shown in Table 1, the Apo2L/TRAIL preparation at a manufacturing scale had a high degree of purity suitable for therapeutic use. The data indicate that the "one-column" step purified Apo2L/TRAIL protein is amenable to crystallization and has a purity comparable to or better than the Apo2L/TRAIL protein purified by the three-column purification method described in Example 1. FIG. 3 shows the effect of salt type on crystallization of a one-column step purified Apo2L/TRAIL. "Poisoning" of crystallization by divalent cations was observed for partially purified Apo2L/TRAIL (FIG. 3).

The biochemical properties of Apo2L/TRAIL were also not adversely impacted by crystallization of the partially purified Apo2L/TRAIL (see Table 1). The data suggest that crystallization of recombinant-expressed Apo2L/TRAIL, when in a partially purified state, can be an effective, efficient and cost-effective means for its purification. Optionally, such crystals can then be used for preparation of dried bulk for storage or controlled release formulations.

Example 3

Method for Recovery and Purification of Apo2L/TRAIL Using Crystallization Including a Second Chromatography Step Following Crystallization (Two-Column Purification)

The harvested whole cell broth derived from *E. coli* (described in Example 1) was adjusted to pH 7.5 with 1.5 M Hepes (or 1.5M Tris). DTT was added to 5 mM to prevent formation of disulfide bonds between the non-covalently bound monomers. Two passes on a homogenizer (Gaulin Corporation, Everett, Mass.) at 6,500 psi burst the *E. coli* cells. The lysate was then diluted one to one with 5 mM DTT in pure water. Once the solution reached room temperature, 5% PEI was added to give a final concentration of 0.2% PEI. PEI caused flocculation of the cell solids, and the material was mixed for at least 30 minutes before centrifuging to allow complete flocculation. After centrifugation, the clarified lysate was filtered using a Cuno Maximizer 30/60SP depth filter (Cuno Incorporated, Meriden, Conn.) Before loading the clarified lysate onto an SP Sepharose column, the pH was adjusted to 7.5 using 1M Na HEPES and the conductivity was adjusted below 9.5 mS/cm using 5 mM DTT in water.

As in the purification method described in Example 2, SP-Sepharose resin, a strong cation exchange resin, was chosen for the primary capture step. The cross-linked agarose matrix with negatively charged functional groups bound to APO2L/TRAIL, while allowing a majority of impurities and APO2L/TRAIL variants to pass through the column. The following buffer conditions were used: 200 mM NaCl, 50 mM HEPES, 0.05% Triton X-100, 1 mM DTT, pH 7.5.

Crystallization of the SP elution pool was achieved by a controlled temperature ramp from 22° C. to 4° C. over a span of four hours. The SP elution pool was sterile filtered and transferred to a temperature controlled tank with good agitation. It was important to ensure that the vessel and the protein solution were free from any particulars prior to crystallization. As the SP elution pool cooled, crystals formed spontaneously with an average chord length of 44 µm as determined by Lasantec's Focused Beam Reflectance Measurement technology. The crystal morphology was hexagonal faces with depth approximately half of the largest chord length. After holding the pool for approximately 1 to 2 hours a 4° C. to allow the crystal growth rate to slow, 50% PEG 3350 was added to give a final concentration of 5% PEG 3350. The addition of PEG 3350 (an anti-solvent) lowered the solubility of APO2L/TRAIL, and promoted further crystal growth.

The crystals formed were then removed by filtration, either batch-wise or continuously. In both cases, the mother liquor was removed, and the crystals washed to remove impurities and residual solvent. Filtration was performed at 2-8° C. The crystal slurry was transferred to a Buchner or Nutsche type filter containing 5-20 µm sintered steel, sintered polypropylene or steel mesh filter either by siphoning or pressurizing the tank containing the crystal slurry. The crystals then were either manually scraped from the filter, or dissolved in a buffer system suitable for the next purification step.

Before loading on a CM-Sepharose column, the crystals were dissolved in 0.5 M arginine-succinate/20 mM TRIS/pH 7.2. Before loading on a Phenyl-Sepharose column, the crystals were dissolved in 0.6 mM $Na_2SO_4$/50 mM TRIS/pH 7.5

The chromatography step following crystallization served to remove the PEG and buffer components from the crystal protein pool, and to provide at least moderate removal of ECP's, endotoxin, dimers, and aggregates.

In one set of experiments, a CM-Sepharose bind-and-elute column was used in this step. Before loading this column, the APO2L/TRAIL crystals were dissolved in formulation buffer, 0.5 M arginine-succinate/20 mM TRIS pH 7.2, and the dissolved pool diluted 5 fold with 20 mM TRIS. The dissolved crystal pool was loaded onto the column and eluted with 125 mM NaCl/50 mM TRIS/1 mM DTT/pH 7.5. The column operation was repeated various times to show consistent recovery (85-95%) and purity.

In another set of experiments, a flow-through column, Phenyl Sepharose HIC, was used. In this case, the crystals were dissolved into 0.6 M $NaSO_4$/50 mM TRIS/1 mM DTT/pH 7.5. The solubility of APO2L/TRAIL was very high in this solution because of the high salt concentration. Three runs consistently had 98% yields and the chromatograms were nearly identical. The level of purity was high, as was observed using the CM-Sepharose bind-and-elute column.

Example 4

Selection of Crystallization Conditions

The SP-Sepharose elution pool from the first chromatography purification step described in Example 3 was cooled to produce crystals and then heated to dissolve the crystals multiple times.

A real time particle size analyzer (Lasentec Focused Beam Reflectance Measurement—FBRM) was used to monitor the crystal chord length and distribution throughout the crystallization process. In the FBRM method, a laser is rotated quickly on a circular path. As the laser passes over the crystal, the beam of light is reflected for a certain duration which is multiplied by the speed of the rotating laser to give a "chord length".

Effect of Temperature Cooling Rate

The FBRM was used to monitor the crystal growth profile as a function of temperature cooling rate. The cooling rate effects the time required for crystallization and the final size distribution. A slow cooling rate supersaturates the solution slowly and the crystal nucleation and growth becomes slow. Quick cooling induces high supersaturation, and many small crystals form.

Figure 4:
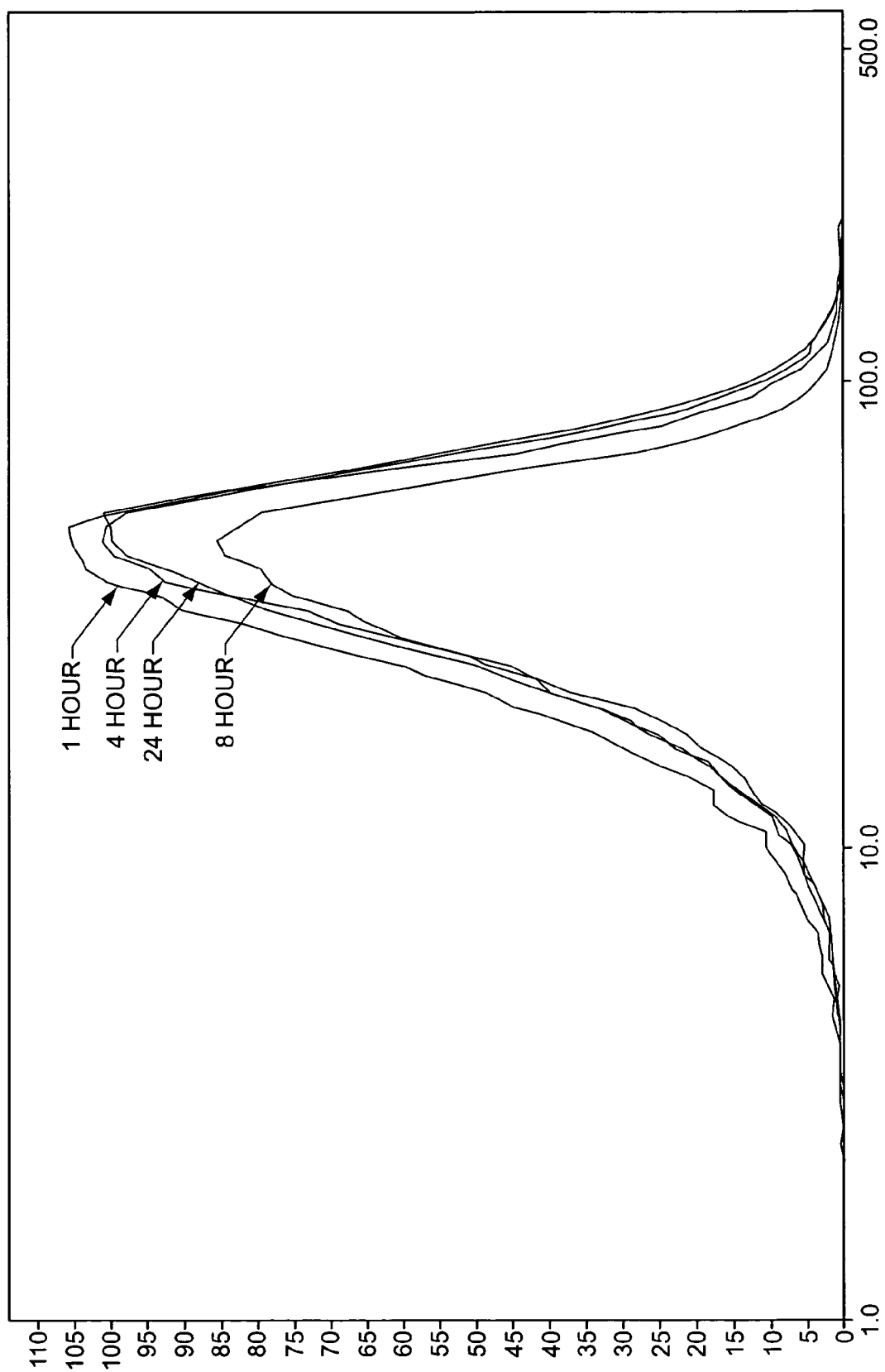
FIG. 4 shows equilibrium crystal size distributions for linear temperature ramps between 22° C. and 2° C. over 1, 4, 8, and 24 hour cooling periods.

A linear temperature ramp from 22° C. to 2° C. over various time periods was investigated. The results of the equilibrium crystal distributions over 1, 4, 8 and 24 hour cooling periods are shown in FIG. 4 and set forth in Table 2.

TABLE 2

| Cooling Time (hour) | Average Size (µm) | # of particles (1–32 µm) | Solubility (g/L) |
| --- | --- | --- | --- |
| 1 | 38 ± 20 | 810 | 0.81 |
| 4 | 43 ± 22 | 560 | 0.74 |
| 8 | 39 ± 18 | 550 | 1.0 |
| 24 | 44 ± 22 | 500 | 0.82 |

A 4-hour cooling rate provided acceptable results.

Effect of Agitation on Crystal Size

Approximately 0.4 L of SP elution buffer was crystallized at three agitation rates. The three rates studies were the minimum required to suspend most of the crystals (100 RPM), the maximum agitation rate before drawings in air bubbles (250 RPM), and an agitation rate in the middle (175 RPM). It was found that crystallization was fastest with the highest agitation rate (250 RMP). The crystal size distribution was very similar for the experiments run at 175 RPM and 250 RPM, and there was no noticeable difference in microscopic images. 100 RPM did not provide enough agitation to completely suspend all the particles. In addition, some aggregation of the crystals was observed. In all cases, the impeller was close to the air surface, and it was easy to drawn in air. In large-scale applications this geometry might change, and higher agitation rates can be used without damaging the protein by exposure to the air-liquid interface.

Anti-solvent Studies

Anti-solvents used in the crystallization process improve crystallization efficiency by lowering the solubility of the protein. Since any protein remaining in solution is lost during filtration, it is important to drive solubility as low as possible during the crystallization reaction.

Anti-solvents were screened by filling 5 mL syringes with APO2L/TRAIL crystals or SP elution pool, and then adding an appropriate amount of anti-solvent. The samples were agitated slowly, over a span of two weeks at both room temperature and at 2-8° C. 1 mL samples were passed through a 0.22 μm filter to remove all protein crystals and then run on an HPLC IEX to determine APO2L/TRAIL Concentration in Solution.

Figure 5:
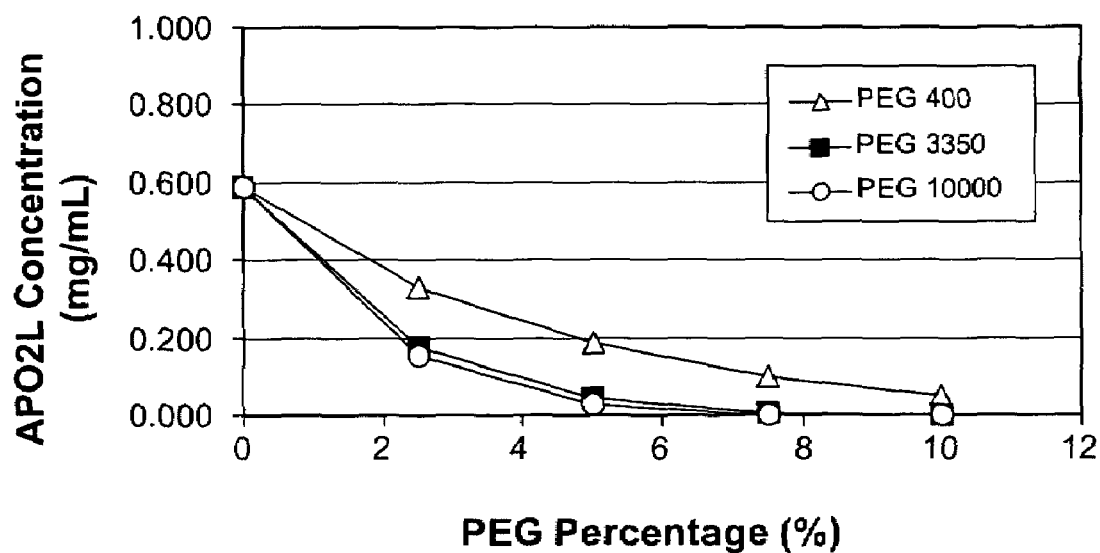
FIG. 5 shows the effect of the addition of PEG on APO2L/TRAIL solubility: 5 days of agitation at 2-8° C.

Polyethylene glycol (PEG) in 400, 3350 and 10000 Da molecular weights (PEG 440, PEG 3350 and PEG 10000, respectively) was tested as an anti-solvent. The APO2L/TRAIL crystals were dissolved in the SP elution buffer (200 mM NaCl, 50 mM HEPES, 0.05% Triton X-100, 1 mM DTT, pH 7.5), and PEG was added. The mixtures were agitated for 5 days at a temperature of 2-8° C. The results shown in FIG. 5 indicate that PEG 3350 and PEG 10000 are superior over PEG 400, and are almost identical in terms of yield improvement. Addition of 5% PEG 3350 improved the theoretical yield from about 85% to about 96% relative to crystallization without the addition of PEG or any other anti-solvent.

Next, the effect of ethanol and isopropyl alcohol on APO2L/TRAIL solubility was examined. Both were found to provide significant yield increases with concentrations between 5% and 10%. The equilibrium APO2L/TRAIL solubility in using these solvents was approximately equivalent to those for PEG.

Other commonly used organic anti-solvents, namely 2-methyl-2,4-pentanedol (MPD), ethylene glycol, and dioxane, were also tested, but offered little or no benefit in terms of reducing APO2L/TRAIL solubility.

Based on these studies, it has been determined that good crystallization results and yields can be achieved by cooling the SP elution pool with a linear temperature ramp between 22° C. and 4° C., using a 4 hour cooling period, and PEG 3350 as an anti-solvent.

Example 5

Two-Column Purification Process using Anti-Solvent in the Crystallization Step

APO2L/TRAIL was purified essentially as described in Example 3, but adding 5% PEG 3350 during crystallization. After crystallization, the material was split into 6 pools. 3 pools were run on a CM-Sepharose column, and 3 pools were run on a Phenyl-Sepharose column. The yield and purity results are give in Table 4 below.

TABLE 4

| Step | Step Yield | ECP (ppm) | LAL (EU/mg) |
|---|---|---|---|
| homogenization | | $1.6 \times 10^6$ | 85.3 |
| SP-Sepharose Column | 89% | 172.90 | 1.9 |
| Crystallization | 96% | 9.1 | 1.9 |
| CM-Sepharose Column (Option #1) | 86% | 1.3 | 1.02 |
| Phenyl-Sepharose Column (Option #2) | 98% | <0.35 | 0.23 |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method of recovering Apo2L/TRAIL from a mixture comprising
   (a) loading the mixture on a cation exchange column;
   (b) washing the cation exchange column with an equilibration buffer whereby non-binding components present in the mixture are removed;
   (c) eluting Apo2L/TRAIL bound to the cation exchange column with an elution buffer;
   (d) crystallizing Apo2L/TRAIL from the eluate obtained in step (c), wherein said crystallization consists of gradually cooling the eluate to a temperature of about 2 to 8° C., in the presence or absence of an anti-solvent, whereby Apo2L/TRAIL is spontaneously precipitated in a crystalline form to yield a mixture of mother liquor and Apo2L/TRAIL crystals, and
   (e) recovering Apo2L/TRAIL from the mixture obtained in step (d) in a purity of at least about 99%.

2. The method of claim 1 wherein the mixture loaded on the cation exchange column is a culture medium or cell lysate of Apo2L/TRAIL producing cells.

3. The method of claim 2 wherein said mixture is the cell lysate of Apo2L/TRAIL producing *E. coli* host cells.

4. The method of claim 3 wherein said lysate is clarified prior to loading on the cation exchange column.

5. The method of claim 1 wherein the eluate obtained in step (c) is subjected to the crystallization step of (d) without additional purification.

6. The method of claim 1 wherein the cation exchange column is an SP-Sepharose column.

7. The method of claim 6 wherein the pH of the mixture loaded on said column is or is adjusted to about 7.5.

8. The method of claim 6 wherein elution of Apo2L/TRAIL is performed in an elution buffer comprising 100-200 mM NaCl or 100-150 mM $Na_2SO_4$ in a buffer adjusting the pH to 7.5-7.8.

9. The method of claim 1 wherein in step (d) the eluate is cooled from a temperature of about 15 to 30° C. to a temperature of about 2 to 8° C. in about 1 to 60 hours.

10. The method of claim 9 wherein in step (d) the eluate is cooled to a temperature of about 2 to 8° C. in about 1 to 8 hours.

11. The method of claim 9 wherein in step (d) the eluate is cooled to a temperature of about 2 to 8° C. in about 1 hour.

12. The method of claim 11 wherein in step (d) the eluate is cooled to a temperature of about 4° C. in about 1 hour.

13. The method of claim 1 wherein the pH of the eluate is or is adjusted to pH 7.0-8.0 prior to crystallization.

14. The method of claim 13 wherein the pH of the eluate is or is adjusted to about 7.3 prior to crystallization.

15. The method of claim 13 wherein the pH of the eluate is or is adjusted to about 7.5-8.0 after crystallization.

16. The method of claim 1 wherein in step (d) the temperature of about 2 to 4° C. is maintained until equilibrium solubility of Apo2L/TRAIL is achieved or nearly achieved.

17. The method of claim 16 wherein in step (d) solubility of Apo2L/TRAIL is decreased by the addition of an anti-solvent.

18. The method of claim 17 wherein said anti-solvent is selected from the group consisting of a polyethylene glycol (PEG), MPD, ethanol, isopropanol, and dioxane.

19. The method of claim 18 wherein the molecular weight of the PEG is between about 400 and about 10,000 daltons.

20. The method of claim 19 wherein the molecular weight of the PEG is 400, 3,350 or 10,000 daltons.

21. The method of claim 1 wherein in step (e) Apo2L/TRAIL is recovered in the form of crystals separated from the mother liquor by filtration or centrifugation or a combination thereof.

22. The method of claim 21 wherein pH of the mother liquor is adjusted to about 8.0 prior to filtration to decrease solubility.

23. The method of claim 1 further comprising the steps of dissolving the Apo2L/TRAIL crystals obtained in step (d) and subjecting the solution obtained to a second chromatographic purification step.

24. The method of claim 23 wherein said second chromatographic purification step is hydrophobic interaction chromatography.

25. The method of claim 24 wherein hydrophobic interaction chromatography is performed on a Phenyl-Sepharose column.

26. The method of claim 23 wherein said second chromatographic purification step is cation exchange chromatography.

27. The method of claim 26 wherein said cation exchange chromatography is performed on an CM-Sepharose or SP-Sepharose column.

28. The method of claim 23 wherein Apo2L/TRAIL is recovered and formulated following said second chromatographic purification step by ultrafiltration-diafiltration.

29. The method of claim 1 wherein said purity is at least about 99.5%.

30. The method of claim 1 wherein said purity is at least about 99.9%.

* * * * *